US009630966B2

(12) United States Patent
Raymon et al.

(10) Patent No.: US 9,630,966 B2
(45) Date of Patent: Apr. 25, 2017

(54) TREATMENT OF CANCER WITH DIHYDROPYRAZINO-PYRAZINES

(71) Applicant: Signal Pharmaceuticals, LLC, San Diego, CA (US)

(72) Inventors: Heather Raymon, San Diego, CA (US); Kristen Mae Hege, Burlingame, CA (US)

(73) Assignee: Signal Pharmaceuticals, LLC, San Diego, CA (US)

(*) Notice: Subject to any disclaimer, the term of this patent is extended or adjusted under 35 U.S.C. 154(b) by 0 days.

(21) Appl. No.: 14/254,004

(22) Filed: Apr. 16, 2014

(65) Prior Publication Data

US 2014/0314674 A1 Oct. 23, 2014

Related U.S. Application Data

(60) Provisional application No. 61/813,071, filed on Apr. 17, 2013.

(51) Int. Cl.
| A61K 49/00 | (2006.01) |
| C07D 487/04 | (2006.01) |
| C12Q 1/68 | (2006.01) |
| A61K 31/4985 | (2006.01) |

(52) U.S. Cl.
CPC ........ *C07D 487/04* (2013.01); *A61K 31/4985* (2013.01); *A61K 49/0004* (2013.01); *C12Q 1/6886* (2013.01)

(58) Field of Classification Search
CPC ...................................................... A61K 49/00
See application file for complete search history.

(56) References Cited

U.S. PATENT DOCUMENTS

| 3,507,866 A | 4/1970 | Jones et al. |
| 3,567,725 A | 3/1971 | Grabowski et al. |
| 4,294,836 A | 10/1981 | Lesher et al. |
| 4,294,837 A | 10/1981 | Lesher et al. |
| 4,309,537 A | 1/1982 | Lesher et al. |
| 4,317,909 A | 3/1982 | Lesher et al. |
| 4,898,872 A | 2/1990 | Campbell et al. |
| 4,963,561 A | 10/1990 | Lesher et al. |
| 5,424,311 A | 6/1995 | Billhardt-Troughton |
| 5,869,659 A | 2/1999 | Stolle et al. |
| 6,031,105 A | 2/2000 | Wright |
| 6,093,728 A | 7/2000 | McMahon et al. |
| 6,372,740 B1 | 4/2002 | Murata et al. |
| 6,566,367 B2 | 5/2003 | Bakthavatchalam et al. |
| 6,791,006 B2 | 9/2004 | Nezu et al. |
| 6,800,436 B1 | 10/2004 | Jenne et al. |
| 6,855,723 B2 | 2/2005 | McMahon et al. |
| 7,608,622 B2 | 10/2009 | Liu et al. |
| 8,372,976 B2 | 2/2013 | Mortensen et al. |
| 8,383,634 B2 | 2/2013 | Mortensen et al. |
| 8,492,381 B2 | 7/2013 | Perrin-Ninkovic et al. |
| 2003/0036652 A1 | 2/2003 | Bakthavatchalam et al. |
| 2003/0162968 A1 | 8/2003 | Ciriillo et al. |
| 2004/0023921 A1 | 2/2004 | Hong et al. |
| 2004/0063658 A1 | 4/2004 | Roberts et al. |
| 2004/0097485 A1 | 5/2004 | Burkitt et al. |
| 2005/0009737 A1 | 1/2005 | Clark |
| 2006/0004014 A1 | 1/2006 | Hoffmann et al. |
| 2006/0135511 A1 | 6/2006 | Burgey |
| 2006/0142269 A1 | 6/2006 | Dykes |
| 2006/0211702 A1 | 9/2006 | Oslob et al. |
| 2007/0036793 A1 | 2/2007 | Hardie et al. |
| 2007/0112005 A1 | 5/2007 | Chen et al. |
| 2008/0194019 A1 | 8/2008 | Cantley et al. |
| 2008/0214580 A1 | 9/2008 | Neagu et al. |
| 2009/0023724 A1 | 1/2009 | Mortensen et al. |
| 2009/0042890 A1 | 2/2009 | Mortensen et al. |
| 2009/0069289 A1 | 3/2009 | Neagu et al. |
| 2009/0163545 A1 | 6/2009 | Goldfard |
| 2009/0181963 A1 | 7/2009 | Dehnhardt et al. |
| 2009/0281075 A1 | 11/2009 | Roughton et al. |
| 2010/0144738 A1 | 6/2010 | Bornmann et al. |
| 2010/0216781 A1 | 8/2010 | Perin-Ninkovic et al. |
| 2010/0249122 A1 | 9/2010 | Kalman |

(Continued)

FOREIGN PATENT DOCUMENTS

| CA | 2 458 699 | 3/2003 |
| DE | 262 026 | 11/1988 |

(Continued)

OTHER PUBLICATIONS

Evanthia Galanis et al. Phase II Trial of Temsirolimus (CCI-779) in Recurrent Glioblastoma Multiforme: A North Central Cancer Treatment Group Study, J. of Clinical Oncology, vol. 23, 5294-5304, 2005.*

Gulati et al., 2009, "Involvement of mTORC1 and mTORC2 in regulation of glioblastoma multiforme growth and motility," International journal of oncology, 35.4 (2009): 731-740.

Wu et al., 2010, "PI3K/Akt/mTOR pathway inhibitors in cancer: a perspective on clinical progress," Current medicinal chemistry, 17.35 (2010): 4326-4341.

(Continued)

*Primary Examiner* — Michael G Hartley
*Assistant Examiner* — Jagadishwar Samala
(74) *Attorney, Agent, or Firm* — Jones Day

(57) ABSTRACT

Provided herein are methods for treating or preventing glioblastoma multiforme (GBM) characterized by O6-methylguanine-DNA methyltransferase (MGMT) expression and/or promoter methylation status, comprising administering an effective amount of a Dihydropyrazino-Pyrazine Compound to a patient having glioblastoma multiforme (GBM) characterized by O6-methylguanine-DNA methyltransferase (MGMT) expression and/or promoter methylation status.

6 Claims, 2 Drawing Sheets

(56) References Cited

U.S. PATENT DOCUMENTS

Figure 1:
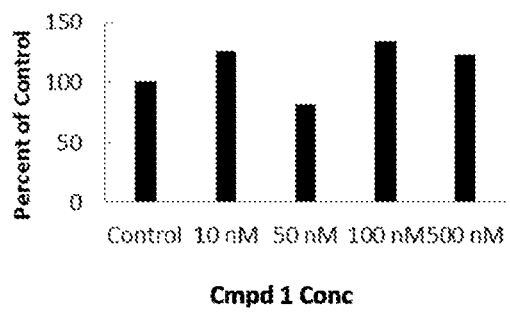
Figure 1:
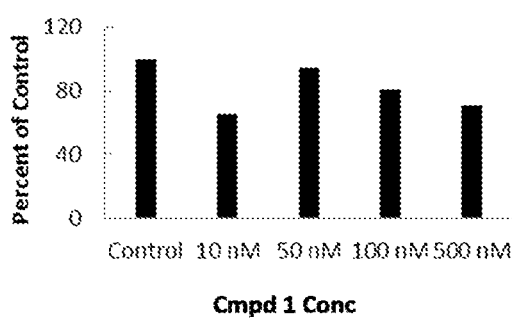
Figure 1:
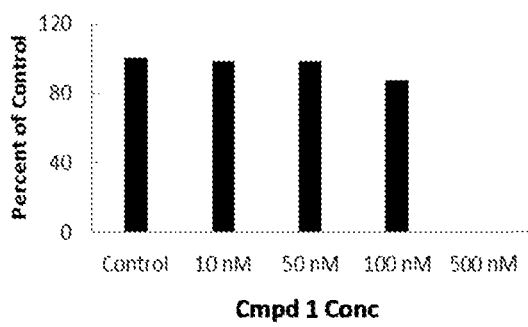
Figure 1:
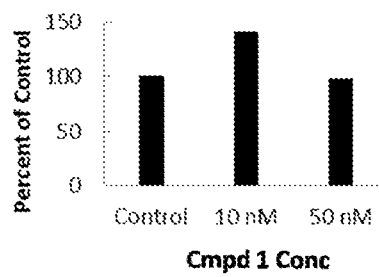

| | | |
|---|---|---|
| 2011/0137028 A1 | 6/2011 | Harris et al. |
| 2011/0257167 A1 | 10/2011 | Chopra et al. |
| 2011/0318336 A1 | 12/2011 | Petricoin, III et al. |
| 2012/0028972 A1 | 2/2012 | Wong et al. |
| 2013/0102613 A1 | 4/2013 | Xu et al. |
| 2013/0142873 A1 | 6/2013 | Assaf et al. |
| 2013/0158023 A1 | 6/2013 | Ning et al. |
| 2013/0225518 A1 | 8/2013 | Xu et al. |
| 2013/0245026 A1 | 9/2013 | Xu et al. |
| 2013/0245027 A1 | 9/2013 | Xu et al. |
| 2013/0245028 A1 | 9/2013 | Xu et al. |
| 2013/0245029 A1 | 9/2013 | Xu et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 99/28459 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/072557 | 9/2003 |
| WO | WO 03/093290 | 11/2003 |
| WO | WO 2004/042002 | 5/2004 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/060404 | 5/2007 |
| WO | WO 2007/066099 | 6/2007 |
| WO | WO 2007/066102 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/064093 | 5/2008 |
| WO | WO 2008/115974 | 9/2008 |
| WO | WO 2008/140947 | 11/2008 |
| WO | WO 2009/007748 | 1/2009 |
| WO | WO 2009/007750 | 1/2009 |
| WO | WO 2009/007751 | 1/2009 |
| WO | WO 2009/052145 | 4/2009 |
| WO | WO 2009/102986 | 8/2009 |
| WO | WO 2010/006072 | 1/2010 |
| WO | WO 2010/062571 | 6/2010 |
| WO | WO 2010/068483 | 6/2010 |
| WO | WO2010062571 | * 6/2010 |
| WO | WO 2011/031965 | 3/2011 |
| WO | WO 2011/053518 | 5/2011 |
| WO | WO 2011/079114 | 6/2011 |
| WO | WO 2011/097333 | 8/2011 |
| WO | WO 2012/016113 | 2/2012 |
| WO | WO 2013/059396 | 4/2013 |
| WO | WO 2013/082344 | 6/2013 |

OTHER PUBLICATIONS

U.S. Appl. No. 14/055,995, filed Oct. 17, 2013, Signal Pharmaceutical, LLC.
U.S. Appl. No. 14/254,001, filed Apr. 16, 2014, Signal Pharmaceutical, LLC.
U.S. Appl. No. 14/254,009, filed Apr. 16, 2014, Signal Pharmaceutical, LLC.
U.S. Appl. No. 14/254,015, filed Apr. 16, 2014, Signal Pharmaceutical, LLC.
U.S. Appl. No. 14/254,017, filed Apr. 16, 2014, Signal Pharmaceutical, LLC.
U.S. Appl. No. 14/254,019, filed Apr. 16, 2014, Signal Pharmaceutical, LLC.
U.S. Appl. No. 14/254,010, filed Apr. 16, 2014, Signal Pharmaceutical, LLC.
U.S. Appl. No. 14/254,020, filed Apr. 16, 2014, Signal Pharmaceutical, LLC.
U.S. Appl. No. 14/254,023, filed Apr. 16, 2014, Signal Pharmaceutical, LLC.
Barlin 1982, "Purine analogs as amplifiers of phleomycin. VII. Some 1H-inidazo[4,5-b]pyrazines and related compound," Australian Journal of Chemistry, vol. 35:2299-2306.
Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org. , pp. 3729-3735.
Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.
Booth et al., 1995, "Synthesis of [1α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.
Booth et al., 2001, "The Reactions of Diaminomaleonitrile with Isocyanates and Either Aldehydes or Ketones Revisited," J. Org Chem, vol. 66:8436-8441.
Booth, et al., 1994, "Synthesis of 4- and 5-Disubstituted 1-Benzylimidazoles, Important Precursors of Purine Analogs," J. of Heterocyclic Chemistry, vol. 31(2):345-50.
Carretero et al. 2010, "Integrative Genomic and Proteomic Analyses Indentity Targets for Lkb1-Deficient Metastatic Lung Tumors," Cancer Cell, vol. 17(6): 547-559.
Chupakhin et al., 2001, "A simple one pot synthesis of condensed 1,2,4-triazines by using the tandem $A_{N\_S N}$ipso and $S_N^{H\_S}{}_N$ipso reactions," J. of Heterocyclic Chemistry, vol. 38(4):901-907.
Cohen, P. 2001, "The role of protein phosphorylation in human health and disease," Eur. J. Biochem,vol. 268:5001-5010.

(56) References Cited

OTHER PUBLICATIONS

Cohen, P. 2002, "Protein kinases—the major drug targets of the twenty-first century?" Nature Reviews/Drug Discovery, vol. 1:309-315.
Cohen, 2005, *Protein Kinase Inhibitors for the Treatment of Disease: The Promise and the Problems*, Handbook of Experimental Pharmacology, Springer Berlin Heidelberg, 167:1-7.
Coish, et al., 2006, "Small molecule inhibitors of IKK kinase activity," Expert Opin. Ther. Patents, vol. 16(1):1-12.
Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.
Dang et al., 1999, "Efficient synthesis of purines and purine nucelosides via an inverse electron demand diels—alder reaction," J. Am Chem Soc., vol. 121(24):5833-5834.
Database CAPLUS Online Chemical Abstracts Service, Columbus, Ohio, Database Accession No. 1951:49974 (XP-002472261) (1951).
Database CAPLUS Online Chemical Abstracts Service, Columbus, Ohio, Database Accession No. 1978:433195 (XP-002472262) (1978).
Database CAPLUS Online Chemical Abstracts Service, Columbus, Ohio, Database Accession No. 1966:26849 (XP-002472263) (1965).
Dornow et al., 1957, "Synthese von2-Oxy-imidazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.
Fabbro et al., 2002, "Protein kinases as targets for anticancer agents: from inhibitors to useful drugs," Pharmacol Ther., 93(2-3):79-98.
Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b] pyridine . . . ," Carcinogenesis, vol. 13(4):629-635.
Gao et al., 2010, "LKB1 inhibits lung cancer progression through lysyl oxidase and extracellular matrix remodeling," Proceedings of the National Academy of Sciences, vol. 107(44): 18892-18897.
Georgakis and Younes, 2006, "From rapi nui to rapamycin: targeting PI3K/Akt/mTOR for cancer therapy," Expert Rev. Anticancer Ther., vol. 6(1):131-140.
Grimmiger et al., 2010, "Targeting non-malignant disorders with tyrosine kinase inhibitors," Nat. Rev. Drug Disc., 9(12):956-970.
Hamad, 2001, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Chin Genet., 66(1):58-62.
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.
Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.
Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.

Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge Microxina species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
PCT Annex to Form PCT/ISA?206 Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Registry File Document for RN 863501-03-5, 863502-39-0 and others (Sep. 20, 2005).
Yuan et al., 2009, "Targeting tumorigenesis: development and use of mTOR inhibitors in cancer therapy," Journal of Hematology & Oncology, Biomed Central Ltd., London UK, vol. 2(1): 45.
Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1):91-99.
Shaw et al., 2009, "LKB1 and AMP-activated protein kinase control of mTOR signalling and growth," Acta. Physiol (Oxf.) 196(1):65-80.
Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-54.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J.Med. Chem., vol. 24(8):941-46.
Wingo et al., 2009, "Somatic LKB1 mutations promote cervical cancer progression," PloS One, 4(4):1-8.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.
Yoneda et al., 1976, "A transformationof 7-azapteridines into 6-azapurines (Imidazo[4,5-e]-as-triazines)," Heterocycles, vol. 4(9):1503-1508.
Yoneda et al., 1978, "Synthesis of imadazo[4,5-e]-as-triazine (6-Azapurine) Deriviatives," Chem & Pharm Bulletin, vol. 26(10):3154-3160.
Zaki et al., 2007, "The synthesis of imidazol[4,5-d]pyridines from a substituted imidazole and acyl or sulfonyl acetonitrile," Tetrahedron, vol. 63(18):3745-3753.
Zhong et al., 2006, "LKB1 mutation in large cell carcinoma of the lung," Cancer Lung, vol. 53(3):285-294.

(56) References Cited

OTHER PUBLICATIONS

Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.

Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.

Hegi et al., 2008, "Correlation of O6-methylguanine methyltransferase (MGMT) promoter methylation with clinical outcomes in glioblastoma and clinical strategies to modulate MGMT activity," Journal of Clinical Oncology 26.25 (2008): 4189-4199.

Hegi et al., 2005, "MGMT gene silencing and benefit from temozolomide in glioblastoma," New England Journal of Medicine 352.10 (2005): 997-1003.

FDA Approval for Temozolomide, 2005, available at http://www.cancer.gov/about-cancer/treatment/drugs/fda-temozolomide (last visited on Feb. 12, 2016).

Glioblastoma multiforme, 2016, available at https://en.wikipedia.org/wiki/Glioblastoma_multiforme (last visited on Feb. 12, 2016).

Hegi et al., 2005, J Clin Oncol. Sep. 1, 2008 26(25):4189-99; FDA Approval for Temozolomide, 2005, available at http://www.cancer.gov/about-cancer/treatment/drugs/fda-temozolomide (last visited on Feb. 12, 2016).

Olson et al., 2014, "The role of cytotoxic chemotherapy in the management of progressive glioblastoma," Journal of neuro-oncology, 118.3(2014): 501-555.

Peinado et al., 2012, Hypomethylation of DNA, Encyclopedia of Cancer, 2012, pp. 1791-1792, available at http://dx.doi.org/10.1007/978-3-642-16483-5_2923 (last visited on Feb. 12, 2016).

\* cited by examiner

A.

B.

C.

D.

US 9,630,966 B2

TREATMENT OF CANCER WITH DIHYDROPYRAZINO-PYRAZINES

This application claims the benefit of U.S. Provisional Application No. 61/813,071, filed Apr. 17, 2013, the entire contents of which are incorporated herein by reference.

1. FIELD

Provided herein are methods for treating or preventing glioblastoma multiforme (GBM) characterized by $O^6$-methylguanine-DNA methyltransferase (MGMT) expression and/or promoter methylation status, comprising administering an effective amount of a Dihydropyrazino-Pyrazine Compound to a patient having glioblastoma multiforme (GBM) characterized by $O^6$-methylguanine-DNA methyltransferase (MGMT) expression and/or promoter methylation status.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001), *Protein Kinase Inhibitors for the Treatment of Disease: The Promise and the Problems*, Handbook of Experimental Pharmacology, Springer Berlin Heidelberg, 167 (2005).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17 (11):1345-1353 (2000). Viral infections and the conditions related thereto have also been associated with the regulation of protein kinases. Park et al. *Cell* 101 (7): 777-787 (2000).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and sirolimus was approved in 1999 for the prophylaxis of renal transplant rejection. Everolimus was approved in 2009 for renal cell carcinoma patients that have progressed on vascular endothelial growth factor receptor inhibitors, in 2010 for subependymal giant cell astrocytoma (SEGA) associated with tuberous sclerosis (TS) in patients who require therapy but are not candidates for surgical resection, and in 2011 for progressive neuroendocrine tumors of pancreatic origin (PNET) in patients with unresectable, locally advanced or metastatic disease. There remains a need for additional TOR kinase inhibitors.

DNA-dependent protein kinase (DNA-PK) is a serine/threonine kinase involved in the repair of DNA double strand breaks (DSBs). DSBs are considered to be the most lethal DNA lesion and occur endogenously or in response to ionizing radiation and chemotherapeutics (for review see Jackson, S. P., Bartek, J. The DNA-damage response in human biology and disease. Nature Rev 2009; 461:1071-1078). If left unrepaired, DSBs will lead to cell cycle arrest and/or cell death (Hoeijmakers, J. H. J. Genome maintenance mechanisms for preventing cancer. Nature 2001; 411: 366-374; van Gent, D. C., Hoeijmakers, J. H., Kanaar, R. Chromosomal stability and the DNA double-stranded break connection. *Nat Rev Genet.* 2001; 2: 196-206). In response to the insult, cells have developed complex mechanisms to repair such breaks and these mechanisms may form the basis of therapeutic resistance. There are two major pathways used to repair DSBs, non-homologous end joining (NHEJ) and homologous recombination (HR). NHEJ brings broken ends of the DNA together and rejoins them without reference to a second template (Collis, S. J., DeWeese, T. L., Jeggo P. A., Parker, A. R. The life and death of DNA-PK. Oncogene 2005; 24: 949-961). In contrast, HR is dependent on the proximity of the sister chromatid which provides a template to mediate faithful repair (Takata, M., Sasaki, M. S., Sonoda, E., Morrison, C., Hashimoto, M., Utsumi, H., et al. Homologous recombination and non-homologous end joining pathways of DNA double-strand break repair have overlapping roles in the maintenance of chromosomal integrity in vertebrate cells. EMBO J. 1998; 17: 5497-5508; Haber, J. E. Partners and pathways repairing a double-strand break. Trends Genet. 2000; 16: 259-264). NHEJ repairs the majority of DSBs. In NHEJ, DSBs are recognized by the Ku protein that binds and then activates the catalytic subunit of DNA-PK. This leads to recruitment and activation of end-processing enzymes, polymerases and DNA ligase IV (Collis, S. J., DeWeese, T. L., Jeggo P. A., Parker, A. R. The life and death of DNA-PK. Oncogene 2005; 24: 949-961). NHEJ is primarily controlled by DNA-PK and thus inhibition of DNA-PK is an attractive approach to modulating the repair response to exogenously induced DSBs. Cells deficient in components of the NHEJ pathway are defective in DSB repair and highly sensitive to ionizing radiation and topoisomerase poisons (reviewed by Smith, G. C. M., Jackson, S. P. The DNA-dependent protein kinase. *Genes Dev* 1999; 13: 916-934; Jeggo, P. A., Caldecott, K., Pidsley, S., Banks, G. R. Sensitivity of Chinese hamster ovary mutants defective in DNA double strand break repair to topoisomerase II inhibitors. Cancer Res 1989; 49: 7057-7063). A DNA-PK inhibitor has been reported to have the same effect of sensitizing cancer cells to therapeutically induced DSBs (Smith, G. C. M., Jackson, S. P. The DNA-dependent protein kinase. *Genes Dev* 1999; 13: 916-934).

Citation or identification of any reference in Section 2 of this application is not to be construed as an admission that the reference is prior art to the present application.

3. SUMMARY

Provided herein are methods for treating or preventing glioblastoma multiforme (GBM) characterized by $O^6$-methylguanine-DNA methyltransferase (MGMT) expression and/or promoter methylation status, comprising administering an effective amount of a Dihydropyrazino-Pyrazine Compound to a patient having GBM characterized by MGMT expression and/or promoter methylation status.

In certain embodiments, provided herein are methods for achieving a Response Assessment for Neuro-Oncology (RANO) Working Group for glioblastoma multiforme of complete response, partial response or stable disease in a patient having glioblastoma multiforme characterized by MGMT expression and/or promoter methylation status, comprising administering an effective amount of a Dihydropyrazino-Pyrazine Compound to said patient.

In some embodiments, the MGMT promoter is hypomethylated. In another embodiment, the MGMT protein is expressed.

In some embodiments, the Dihydropyrazino-Pyrazine Compound is a compound as described herein.

The present embodiments can be understood more fully by reference to the detailed description and examples, which are intended to exemplify non-limiting embodiments.

4. BRIEF DESCRIPTION OF THE DRAWINGS

FIG. 1: The sphere re-formation assay demonstrates that Compound 1 does not specifically target sphere-initiating cells in patient-derived GBM cell cultures. Tumorsphere lines A) 206 B) 217 C) 254 D) 282 were dissociated and plated as single cells at a density of 50,000 cells/ml of tumorsphere media in a total of 10 mL per T-25 cell culture flask and 5 flasks per cell line. Each flask was treated with a single concentration of Compound 1 for 7 days. Cells that survived the 7 day treatment were washed free of Compound 1, dissociated into single cells, and plated at clonal tumorsphere density in 96 well plates. 60 wells were plated from each flask of cells. Tumorspheres were allowed to grow until they achieved at least 60 microns in diameter before they were counted. The percentage of tumorsphere formation was calculated as the number of tumorspheres counted divided by the number of cells seeded times the plating efficiency of the control.

Figure 2:
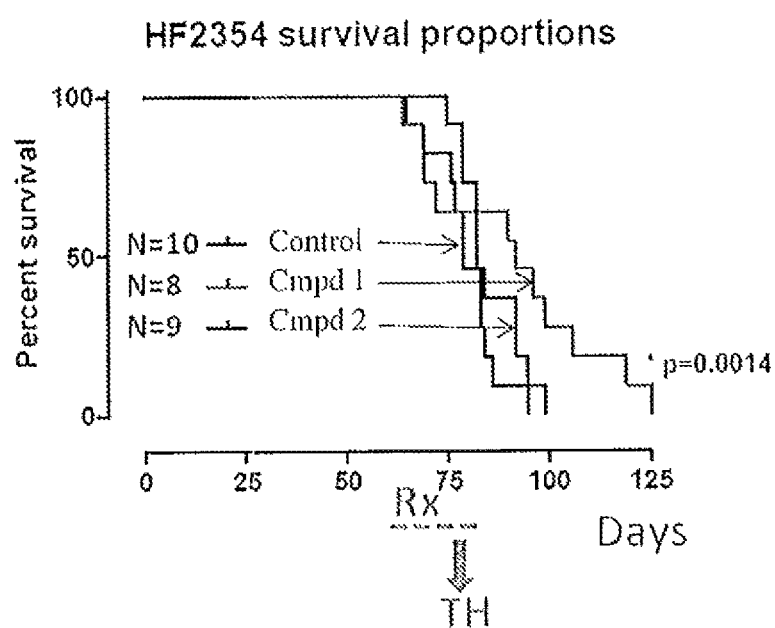

FIG. 2: Kaplan-Meier survival analysis for HF2354 PDX line (end of study). Treatment schedule for survival (Rx) and target hit (TH) are indicated.

5. DETAILED DESCRIPTION

5.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturared alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_2$CH$_3$), among others. An alkyl group can be substituted or unsubstituted. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

An "alkenyl" group is a straight chain or branched non-cyclic hydrocarbon having from 2 to 10 carbon atoms, typically from 2 to 8 carbon atoms, and including at least one carbon-carbon double bond. Representative straight chain and branched (C$_2$-C$_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

A "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyrdine-3-yl methyl, (tetrahydro-2H-pyran-4-yl)methyl, (tetrahydro-2H-pyran-4-yl)ethyl, tetrahydrofuran-2-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —NH$_2$.

A "hydroxylamine" group is a radical of the formula: —N(R#)OH or —NHOH, wherein R# is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: —N(R#)O-alkyl or —NHO-alkyl, wherein R# is as defined above.

An "aralkoxyamine" group is a radical of the formula: —N(R#)O-aryl or —NHO-aryl, wherein R# is as defined above.

An "alkylamine" group is a radical of the formula: —NH-alkyl or —N(alkyl)$_2$, wherein each alkyl is independently as defined above.

An "aminocarbonyl" group is a radical of the formula: —C(=O)N(R$^{14}$)$_2$, —C(=O)NH(R#), or —C(=O)NH$_2$, wherein each R# is as defined above.

An "acylamino" group is a radical of the formula: —NHC(=O)(R#) or —N(alkyl)C(=O)(R#), wherein each alkyl and R# are independently as defined above.

An "O(alkyl)aminocarbonyl" group is a radical of the formula: —O(alkyl)C(=O)N(R$^{14}$)$_2$, —O(alkyl)C(=O)NH(R#) or —O(alkyl)C(=O)NH$_2$, wherein each R# is independently as defined above.

An "N-oxide" group is a radical of the formula: —N$^+$—O$^-$.

A "carboxy" group is a radical of the formula: —C(=O)OH.

A "ketone" group is a radical of the formula: —C(=O)(R#), wherein R# is as defined above.

An "aldehyde" group is a radical of the formula: —CH(=O).

An "ester" group is a radical of the formula: —C(=O)O(R#) or —OC(=O)(R#), wherein R# is as defined above.

A "urea" group is a radical of the formula: —N(alkyl)C(=O)N(R#), —N(alkyl)C(=O)NH(R#), —N(alkyl)C(=O)NH$_2$, —NHC(=O)N(R$^{14}$)$_2$, —NHC(=O)NH(R#), or —NHC(=O)NH$_2$#, wherein each alkyl and R# are independently as defined above.

An "imine" group is a radical of the formula: —N=C(R#)$_2$ or —C(R#)=N(R#), wherein each R# is independently as defined above.

An "imide" group is a radical of the formula: —C(=O)N(R#)C(=O)(R#) or —N((C=O)(R#))$_2$, wherein each R# is independently as defined above.

A "urethane" group is a radical of the formula: —OC(=O)N(R#)$_2$, —OC(=O)NH(R#), —N(R#)C(=O)O(R#), or —NHC(=O)O(R#), wherein each R# is independently as defined above.

An "amidine" group is a radical of the formula: —C(=N(R#))N(R#)$_2$, —C(=N(R#))NH(R#), —C(=N(R#))NH$_2$, —C(=NH)N(R#)$_2$, —C(=NH)NH(R#), —C(=NH)NH$_2$, —N=C(R#)N(R#)$_2$, —N=C(R#)NH(R#), —N=C(R#)NH$_2$, —N(R#)C(R#)=N(R#), —NHC(R#)=N(R#), —N(R#)C(R#)=NH, or —NHC(R#)=NH, wherein each R# is independently as defined above.

A "guanidine" group is a radical of the formula: —N(R#)C(=N(R#))N(R#)$_2$, —NHC(=N(R#))N(R#)$_2$, —N(R#)C(=NH)N(R#)$_2$, —N(R#)C(=N(R#))NH(R#), —N(R#)C(=N(R#))NH$_2$, —NHC(=NH)N(R#)$_2$, —NHC(=N(R#))NH(R#), —NHC(=N(R#))NH$_2$, —NHC(=NH)NH(R#), —NHC(=NH)NH$_2$, —N=C(N(R#)$_2$)$_2$, —N=C(NH(R#))$_2$, or —N=C(NH$_2$)$_2$, wherein each R# is independently as defined above.

An "enamine" group is a radical of the formula: —N(R#)C(R#)=C(R#)$_2$, —NHC(R#)=C(R#)$_2$, —C(N(R#)$_2$)=C(R#)$_2$, —C(NH(R#))=C(R#)$_2$, —C(NH$_2$)=C(R#)$_2$, —C(R#)=C(R#)(N(R#)$_2$), C(R#)=C(R#)(NH(R#)) or —C(R#)=C(R#)(NH$_2$), wherein each R# is independently as defined above.

An "oxime" group is a radical of the formula: —C(=NO(R#))(R#), —C(=NOH)(R#), —CH(=NO(R#)), or —CH(=NOH), wherein each R# is independently as defined above.

A "hydrazide" group is a radical of the formula: —C(=O)N(R#)N(R#)$_2$, —C(=O)NHN(R#)$_2$, —C(=O)N(R#)NH(R#), —C(=O)N(R#)NH$_2$, —C(=O)NHNH(R#)$_2$, or —C(=O)NHNH$_2$, wherein each R# is independently as defined above.

A "hydrazine" group is a radical of the formula: —N(R#)N(R#)$_2$, —NHN(R#)$_2$, —N(R#)NH(R#), —N(R#)NH$_2$, —NHNH(R#)$_2$, or —NHNH$_2$, wherein each R# is independently as defined above.

A "hydrazone" group is a radical of the formula: —C(=N—N(R#)$_2$)(R#)$_2$, —C(=N—NH(R#))(R#)$_2$, —C(=N—NH$_2$)(R#)$_2$, —N(R#)(N=C(R#)$_2$), or —NH(N=C(R#)$_2$), wherein each R# is independently as defined above.

An "azide" group is a radical of the formula: —N$_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; —S(R#), wherein R# is as defined above.

A "thiocarbonyl" group is a radical of the formula: —C(=S)(R#), wherein R# is as defined above.

A "sulfinyl" group is a radical of the formula: —S(=O)(R#), wherein R# is as defined above.

A "sulfone" group is a radical of the formula: —S(=O)$_2$(R#), wherein R# is as defined above.

A "sulfonylamino" group is a radical of the formula: —NHSO$_2$(R#) or —N(alkyl)SO$_2$(R#), wherein each alkyl and R# are defined above.

A "sulfonamide" group is a radical of the formula: —S(=O)$_2$N(R#)$_2$, or —S(=O)$_2$NH(R#), or —S(=O)$_2$NH$_2$, wherein each R# is independently as defined above.

A "phosphonate" group is a radical of the formula: —P(=O)(O(R#))$_2$, —P(=O)(OH)$_2$, —OP(=O)(O(R#))(R#), or —OP(=O)(OH)(R#), wherein each R# is independently as defined above.

A "phosphine" group is a radical of the formula: —P(R#)$_2$, wherein each R# is independently as defined above.

When the groups described herein, with the exception of alkyl group are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl);

monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Dihydropyrazino-Pyrazine Compound include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "clathrate" means a Dihydropyrazino-Pyrazine Compound, or a salt thereof, in the form of a crystal lattice that contains spaces (e.g., channels) that have a guest molecule (e.g., a solvent or water) trapped within or a crystal lattice wherein a Dihydropyrazino-Pyrazine Compound is a guest molecule.

As used herein and unless otherwise indicated, the term "solvate" means a Dihydropyrazino-Pyrazine Compound, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a Dihydropyrazino-Pyrazine Compound, or a salt thereof, that further includes a stoichiometric or non-stoichiometric amount of water bound by non-covalent intermolecular forces.

As used herein and unless otherwise indicated, the term "prodrug" means a Dihydropyrazino-Pyrazine Compound derivative that can hydrolyze, oxidize, or otherwise react under biological conditions (in vitro or in vivo) to provide an active compound, particularly a Dihydropyrazino-Pyrazine Compound. Examples of prodrugs include, but are not limited to, derivatives and metabolites of a Dihydropyrazino-Pyrazine Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a Dihydropyrazino-Pyrazine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Dihydropyrazino-Pyrazine Compounds can have chiral centers and can occur as racemates, individual enantiomers or diastereomers, and mixtures thereof. All such isomeric forms are included within the embodiments disclosed herein, including mixtures thereof. The use of stereomerically pure forms of such Dihydropyrazino-Pyrazine Compounds, as well as the use of mixtures of those forms are encompassed by the embodiments disclosed herein. For example, mixtures comprising equal or unequal amounts of the enantiomers of a particular Dihydropyrazino-Pyrazine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Dihydropyrazino-Pyrazine Compounds can include E and Z isomers, or a mixture thereof, and cis and trans isomers or a mixture thereof. In certain embodiments, the Dihydropyrazino-Pyrazine Compounds are isolated as either the cis or trans isomer. In other embodiments, the Dihydropyrazino-Pyrazine Compounds are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

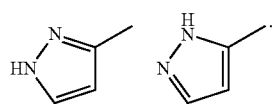

As readily understood by one skilled in the art, a wide variety of functional groups and other structures may exhibit tautomerism and all tautomers of the Dihydropyrazino-Pyrazine Compounds are within the scope of the present invention.

It should also be noted the Dihydropyrazino-Pyrazine Compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Dihydropyrazino-Pyrazine Compounds as described herein, whether radioactive or not, are intended to be encompassed within the scope of the embodiments provided herein. In some embodiments, there are provided isotopologues of the Dihydropyrazino-Pyrazine Compounds, for example, the isotopologues are deuterium, carbon-13, or nitrogen-15 enriched Dihydropyrazino-Pyrazine Compounds.

It should be noted that if there is a discrepancy between a depicted structure and a name for that structure, the depicted structure is to be accorded more weight.

$O^6$-Alkyl-guanine is the major carcinogenic lesion in DNA induced by alkylating mutagens. This DNA adduct is removed by the repair protein, $O^6$-methylguanine-DNA methyltransferase (MGMT), encoded by the MGMT gene. The protein is not a true enzyme since it accepts the alkyl group from the lesion in a stoichiometric reaction and the active enzyme is not regenerated after it is alkylated. The methyl-acceptor residue in the protein is cysteine (Kaina B, Christmann M, Naumann S, Roos W P (August 2007). *DNA Repair (Amst.)* 6 (8): 1079-99). Diminished MGMT protein expression due to methylation of CpG sites in the promoter region of the MGMT gene allows accumulation of alkyl-guanine DNA which, following incorrect base pairing with thymine, triggers DNA damage signaling and cell death. MGMT promoter methylation is the key mechanism of MGMT gene silencing.

As used herein "MGMT protein expression status" refers to the expression of MGMT protein. In one embodiment, the MGMT protein is expressed. In one embodiment, MGMT protein expression is determined by, for example immunohistochemistry or Western Blot.

As used herein "MGMT promoter methylation status" refers to methylation of the MGMT gene promoter. In one embodiment, the promoter is hypomethylated. In one embodiment, the MGMT promoter methylation status is determined by, for example, methylation-specific PCR (MSP) and bisulfite sequencing (BiSEQ) of 24 neighboring CpG sites.

"Treating" as used herein, means an alleviation, in whole or in part, of GBM characterized by MGMT expression and/or promoter methylation status, or a symptom thereof, or slowing, or halting of further progression or worsening of GBM characterized by MGMT expression and/or promoter methylation status or a symptom thereof. In one embodiment, the MGMT promoter is hypomethylated. In another embodiment, the MGMT protein is expressed.

"Preventing" as used herein, means the prevention of the onset, recurrence or spread, in whole or in part, of GBM characterized by MGMT protein expression and/or promoter methylation status or a symptom thereof. In one embodiment, the MGMT promoter is hypomethylated. In another embodiment, the MGMT protein is expressed.

The term "effective amount" in connection with a Dihydropyrazino-Pyrazine Compound means an amount capable of alleviating, in whole or in part, symptoms associated with GBM characterized by MGMT expression and/or promoter methylation status, or slowing or halting further progression or worsening of those symptoms, or treating or preventing GBM characterized by MGMT protein expression and/or promoter methylation status. The effective amount of the Dihydropyrazino-Pyrazine Compound, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of a Dihydropyrazino-Pyrazine Compound disclosed herein may vary depending on the severity of the indication being treated.

In one embodiment, the patient is a human having GBM characterized by MGMT expression and/or promoter methylation status. In one embodiment, the MGMT promoter is hypomethylated. In another embodiment, the MGMT protein is expressed.

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a "patient" or "subject" is a human having GBM characterized by MGMT expression and/or promoter methylation status. In one embodiment, a patient is a human having histologically or cytologically-confirmed GBM characterized by MGMT expression and/or promoter methylation status, including subjects who have progressed on (or not been able to tolerate) standard anticancer therapy or for whom no standard anticancer therapy exists. In one such embodiment, the standard anticancer therapy is Temozolomide.

In the context of GBM characterized by MGMT expression and/or promoter methylation status, treatment may be assessed by inhibition of disease progression, inhibition of tumor growth, reduction of primary and/or secondary tumor(s), relief of tumor-related symptoms, improvement in quality of life, delayed appearance of primary and/or secondary tumor(s), slowed development of primary and/or secondary tumor(s), decreased occurrence of primary and/or secondary tumor(s), slowed or decreased severity of secondary effects of disease, arrested tumor growth and/or regression of tumors, among others. In certain embodiments, treatment of GBM characterized by MGMT protein expression and/or promoter methylation status may be assessed by the inhibition of phosphorylation of S6RP, 4E-BP1 and/or AKT in circulating blood and/or tumor cells and/or skin biopsies or tumor biopsies/aspirates, before, during and/or after treatment with a Dihydropyrazino-Pyrazine Compound. In other embodiments, treatment of GBM characterized by MGMT protein expression and/or promoter methylation status may be assessed by the inhibition of DNA-dependent protein kinase (DNA-PK) activity in skin samples and/or tumor biopsies/aspirates, such as by assessment of the amount of pDNA-PK S2056 as a biomarker for DNA damage pathways, before, during, and/or after Dihydropyrazino-Pyrazine Compound treatment. In one embodiment, the skin sample is irradiated by UV light. In the extreme, complete inhibition, is referred to herein as prevention or chemoprevention. In this context, the term "prevention" includes either preventing the onset of clinically evident GBM characterized by MGMT protein expression and/or promoter methylation status altogether or preventing the onset of a preclinically evident stage of GBM carcinoma characterized by MGMT protein expression and/or promoter methylation status. Also intended to be encompassed by this definition is the prevention of transformation into malignant cells or to arrest or reverse the progression of premalignant cells to malignant cells. This includes prophylactic treatment of those at risk of developing GBM characterized by MGMT protein expression and/or promoter methylation status.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery [FLAIR] images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and nonmeasurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

In certain embodiments, treatment of a cancer may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor, for example, a Dihydropyrazino-Pyrazine Compound. For example, the inhibition of phosphorylation of S6RP, 4E-BP1, AKT and/or DNA-PK is assessed in B-cells, T-cells and/or monocytes.

In other embodiments, treatment of a cancer may be assessed by the inhibition of DNA-dependent protein kinase (DNA-PK) activity in skin samples and/or tumor biopsies/aspirates, such as by assessment of the amount of pDNA-PK S2056 as a biomarker for DNA damage pathways, before, during, and/or after TOR kinase inhibitor treatment, for example, a Dihydropyrazino-Pyrazine Compound. In one embodiment, the skin sample is irradiated by UV light.

In the extreme, complete inhibition, is referred to herein as prevention or chemoprevention. In this context, the term "prevention" includes either preventing the onset of clinically evident GBM characterized by MGMT methylation altogether or preventing the onset of a preclinically evident stage of GBM characterized by MGMT methylation. Also intended to be encompassed by this definition is the prevention of transformation into malignant cells or to arrest or reverse the progression of premalignant cells to malignant cells. This includes prophylactic treatment of those at risk of developing GBM characterized by MGMT methylation.

5.2 Dihydropyrazino-Pyrazines

The compounds provided herein are TOR kinase inhibitors, generally referred to as "Dihydropyrazino-Pyrazine Compound(s)." In one aspect, the TOR kinase inhibitors do not include rapamycin or rapamycin analogs (rapalogs).

In one embodiment, the Dihydropyrazino-Pyrazine Compounds include compounds having the following formula (I):

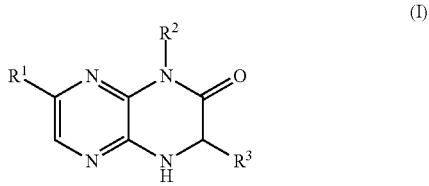

and pharmaceutically acceptable salts, clathrates, solvates, stereoisomers, tautomers, prodrugs, metabolites and isotopologues thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl, wherein in certain embodiments, the Dihydropyrazino-Pyrazine Compounds do not include 7-(4-hydroxyphenyl)-1-(3-methoxybenzyl)-3,4-dihydropyrazino[2,3-b]pyrazin-2(1H)-one, depicted below:

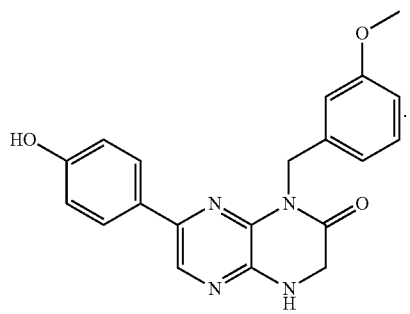 [SMILES: COc1cccc(CN2C(=O)CNc3ncc(-c4ccc(O)cc4)nc32)c1]

In some embodiments of compounds of formula (I), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —NR$_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —NR$_2$, wherein R is independently H, or a substituted or unsubstituted $C_{1-4}$ alkyl.

In some embodiments, $R^1$ is

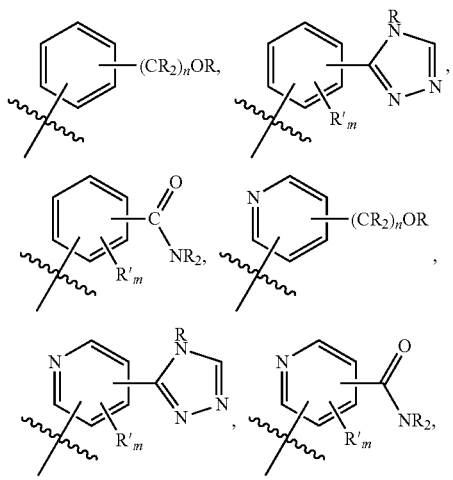

-continued

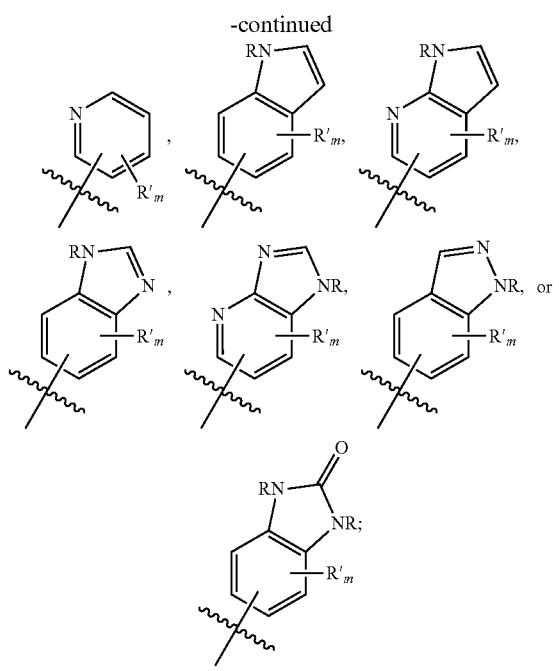

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —$NR_2$; m is 0-3; and n is 0-3. It will be understood by those skilled in the art that any of the substituents R' may be attached to any suitable atom of any of the rings in the fused ring systems.

In some embodiments of compounds of formula (I), $R^1$ is

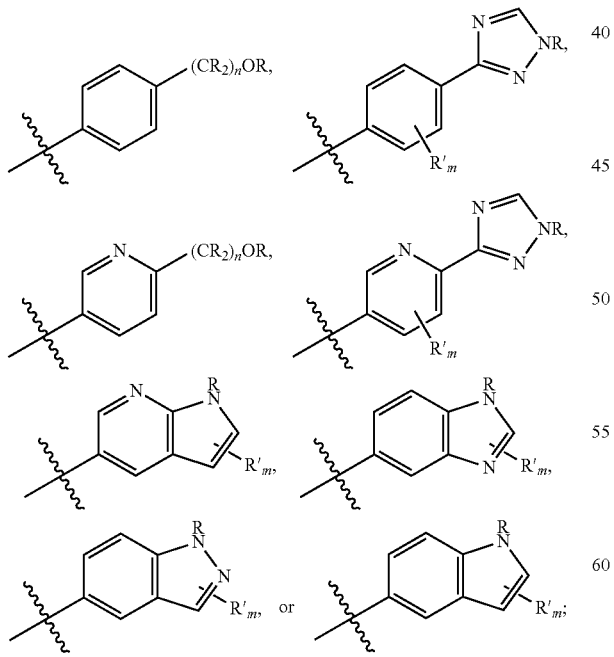

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —$NR_2$; m is 0-3; and n is 0-3.

In some embodiments of compounds of formula (I), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

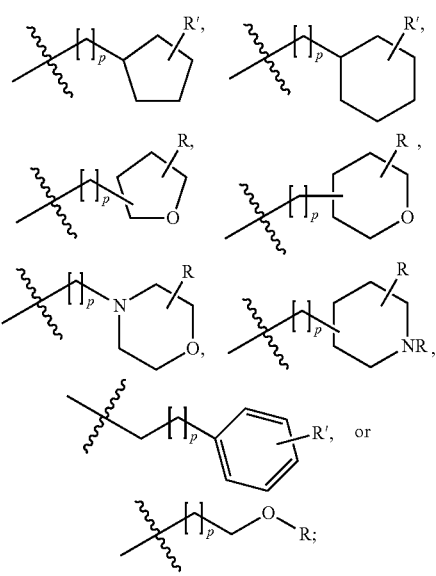

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (I), $R^2$ is H, $C_{1-4}$ alkyl, ($C_{1-4}$alkyl)(OR),

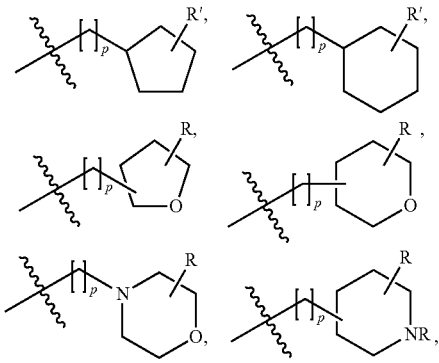

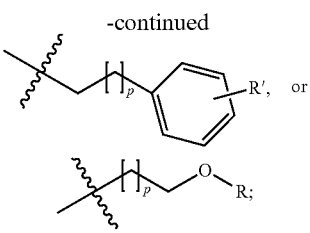

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (I), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —$NR_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In one embodiment of compounds of formula (I), $R^1$ is phenyl, pyridyl, pyrimidyl, benzimidazolyl, 1H-pyrrolo[2,3-b]pyridyl, indazolyl, or indolyl, each optionally substituted. In some such embodiments, $R^1$ is phenyl substituted with one or more substituents independently selected from the group consisting of substituted or unsubstituted $C_{1-8}$ alkyl, substituted or unsubstituted heterocyclyl (for example, substituted or unsubstituted triazolyl), or halogen. In some other such embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, hydroxyalkyl, —OR, and —$NR_2$, wherein each R is independently H, or a substituted or unsubstituted $C_{1-4}$ alkyl. In some other such embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments of compounds of formula (I), $R^2$ is H, substituted or unsubstituted $C_{1-8}$ alkyl, substituted or unsubstituted cycloalkyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. In some such embodiments, $R^2$ is H, methyl, ethyl, isopropyl, cyclohexyl, ($C_{1-4}$ alkyl)-phenyl, ($C_{1-4}$ alkyl)-cyclohexyl, (or ($C_{1-4}$ alkyl)-tetrahydropyranyl, each optionally substituted.

In some such embodiments of $R^2$, $R^1$ is phenyl, pyridyl, pyrimidyl, benzimidazolyl, 1H-pyrrolo[2,3-b]pyridyl, indazolyl, or indolyl, each optionally substituted. For example, $R^1$ is phenyl, substituted with one or more substituents independently selected from the group consisting of substituted or unsubstituted $C_{1-8}$ alkyl, substituted or unsubstituted heterocyclyl (for example, substituted or unsubstituted triazolyl), or halogen. In some other such embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, hydroxyalkyl, —OR, and —$NR_2$, wherein each R is independently H, or a substituted or unsubstituted $C_{1-4}$ alkyl.

In certain embodiments, the compounds of formula (I) have an $R^1$ group set forth herein and an $R^2$ group set forth herein.

In some embodiments of compounds of formula (I), the compound inhibits TOR kinase. In other embodiments of compounds of formula (I), the compound inhibits DNA-PK. In certain embodiments of compounds of formula (I), the compound inhibits both TOR kinase and DNA-PK.

In some embodiments of compounds of formula (I), the compound at a concentration of 10 μM inhibits TOR kinase, DNA-PK, PI3K, or a combination thereof by at least about 50%. Compounds of formula (I) may be shown to be inhibitors of the kinases above in any suitable assay system.

Representative Dihydropyrazino-Pyrazine Compounds of formula (I) include:

7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-methoxycyclohexyl)-3,4-dihydropyrazino[2,3-b]pyrazin-2(1H)-one;

7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;

1-ethyl-7-(1H-pyrrolo[3,2-b]pyridin-5-yl)-3,4-dihydropyrazino[2,3-b]pyrazin-2(1H)-one;

7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;

7-(1H-benzo[d]imidazol-4-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;

7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;

7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;

7-(6-(1H-1,2,4-triazol-3-yl)pyridin-3-yl)-1-(2-methoxyethyl)-3,4-dihydropyrazino[2,3-b]pyrazin-2(1H)-one;

7-(6-(1H-1,2,4-triazol-3-yl)pyridin-3-yl)-1-ethyl-3,4-dihydropyrazino[2,3-b]pyrazin-2(1H)-one;

7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;

7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;

7-(1H-indol-4-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(trans-4-hydroxycyclohexyl)-3,4-dihydropyrazino[2,3-b]pyrazin-2(1H)-one;

7-(6-(1H-1,2,4-triazol-3-yl)pyridin-3-yl)-1-(trans-4-methoxycyclohexyl)-3,4-dihydropyrazino[2,3-b]pyrazin-2(1H)-one;

7-(6-(1H-1,2,4-triazol-3-yl)pyridin-3-yl)-1-isopropyl-3,4-dihydropyrazino[2,3-b]pyrazin-2(1H)-one;

7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;

7-(5-fluoro-2-methyl-4-(1H-1,2,4-triazol-3-yl)phenyl)-1-isopropyl-3,4-dihydropyrazino[2,3-b]pyrazin-2(1H)-one;

1-ethyl-7-(5-fluoro-2-methyl-4-(1H-1,2,4-triazol-3-yl)phenyl)-3,4-dihydropyrazino[2,3-b]pyrazin-2(1H)-one;

7-(2-hydroxypyridin-4-yl)-1-(2-(tetrahydro-2H-pyran-4-yl)ethyl)-3,4-dihydropyrazino[2,3-b]pyrazin-2(1H)-one;

1-isopropyl-7-(4-methyl-6-(1H-1,2,4-triazol-3-yl)pyridin-3-yl)-3,4-dihydropyrazino[2,3-b]pyrazin-2(1H)-one;

5-(8-isopropyl-7-oxo-5,6,7,8-tetrahydropyrazino[2,3-b]pyrazin-2-yl)-4-methylpicolinamide;

7-(1H-indazol-4-yl)-1-(2-(tetrahydro-2H-pyran-4-yl)ethyl)-3,4-dihydropyrazino[2,3-b]pyrazin-2(1H)-one;

7-(2-aminopyrimidin-5-yl)-1-(2-(tetrahydro-2H-pyran-4-yl)ethyl)-3,4-dihydropyrazino[2,3-b]pyrazin-2(1H)-one;

7-(2-aminopyridin-4-yl)-1-(2-(tetrahydro-2H-pyran-4-yl)ethyl)-3,4-dihydropyrazino[2,3-b]pyrazin-2(1H)-one;

7-(6-(methylamino)pyridin-3-yl)-1-(2-(tetrahydro-2H-pyran-4-yl)ethyl)-3,4-dihydropyrazino[2,3-b]pyrazin-2(1H)-one;

7-(6-hydroxypyridin-3-yl)-1-(2-(tetrahydro-2H-pyran-4-yl)ethyl)-3,4-dihydropyrazino[2,3-b]pyrazin-2(1H)-one;

7-(4-(1H-pyrazol-3-yl)phenyl)-1-(2-methoxyethyl)-3,4-dihydropyrazino[2,3-b]pyrazin-2(1H)-one;

7-(pyridin-3-yl)-1-(2-(tetrahydro-2H-pyran-4-yl)ethyl)-3,4-dihydropyrazino[2,3-b]pyrazin-2(1H)-one;

7-(1H-indazol-4-yl)-1-(2-methoxyethyl)-3,4-dihydropyrazino[2,3-b]pyrazin-2(1H)-one;

7-(1H-indazol-6-yl)-1-(2-methoxyethyl)-3,4-dihydropyrazino[2,3-b]pyrazin-2(1H)-one;

7-(pyrimidin-5-yl)-1-(2-(tetrahydro-2H-pyran-4-yl)ethyl)-3,4-dihydropyrazino[2,3-b]pyrazin-2(1H)-one;

7-(6-methoxypyridin-3-yl)-1-(2-(tetrahydro-2H-pyran-4-yl)ethyl)-3,4-dihydropyrazino[2,3-b]pyrazin-2(1H)-one;

1-(2-methoxyethyl)-7-(1H-pyrrolo[2,3-b]pyridin-5-yl)-3,4-dihydropyrazino[2,3-b]pyrazin-2(1H)-one;

1-ethyl-7-(1H-pyrrolo[2,3-b]pyridin-5-yl)-3,4-dihydropyrazino[2,3-b]pyrazin-2(1H)-one;

1-ethyl-7-(1H-indazol-4-yl)-3,4-dihydropyrazino[2,3-b]pyrazin-2(1H)-one;

7-(pyridin-4-yl)-1-(2-(tetrahydro-2H-pyran-4-yl)ethyl)-3,4-dihydropyrazino[2,3-b]pyrazin-2(1H)-one;

7-(6-aminopyridin-3-yl)-1-(2-(tetrahydro-2H-pyran-4-yl)ethyl)-3,4-dihydropyrazino[2,3-b]pyrazin-2(1H)-one;

1-methyl-7-(2-methyl-6-(4H-1,2,4-triazol-3-yl)pyridin-3-yl)-3,4-dihydropyrazino[2,3-b]pyrazin-2(1H)-one;

2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;

4-methyl-5-(7-oxo-8-((tetrahydro-2H-pyran-4-yl)methyl)-5,6,7,8-tetrahydropyrazino[2,3-b]pyrazin-2-yl)picolinamide;

5-(8-((cis-4-methoxycyclohexyl)methyl)-7-oxo-5,6,7,8-tetrahydropyrazino[2,3-b]pyrazin-2-yl)-4-methylpicolinamide;

7-(1H-pyrazol-4-yl)-1-(2-(tetrahydro-2H-pyran-4-yl)ethyl)-3,4-dihydropyrazino[2,3-b]pyrazin-2(1H)-one;

1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;

3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;

1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;

3-(7-oxo-8-(2-(tetrahydro-2H-pyran-4-yl)ethyl)-5,6,7,8-tetrahydropyrazino[2,3-b]pyrazin-2-yl)benzamide;

5-(8-((trans-4-methoxycyclohexyl)methyl)-7-oxo-5,6,7,8-tetrahydropyrazino[2,3-b]pyrazin-2-yl)-4-methylpicolinamide;

3-((7-(6-(2-hydroxypropan-2-yl)pyridin-3-yl)-2-oxo-3,4-dihydropyrazino[2,3-b]pyrazin-1(2H)-yl)methyl)benzonitrile;

7-(6-(2-hydroxypropan-2-yl)pyridin-3-yl)-1-((1R,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3S)-3-methoxycyclopentyl)-3,4-dihydropyrazino[2,3-b]pyrazin-2(1H)-one;

7-(6-(2-hydroxypropan-2-yl)pyridin-3-yl)-1-((1R,3S)-3-methoxycyclopentyl)-3,4-dihydropyrazino[2,3-b]pyrazin-2(1H)-one;

7-(1H-indazol-6-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(2-morpholinoethyl)-3,4-dihydropyrazino[2,3-b]pyrazin-2(1H)-one;

1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(2-morpholinoethyl)-3,4-dihydropyrazino[2,3-b]pyrazin-2(1H)-one;
1-isopropyl-7-(2-methyl-6-(4H-1,2,4-triazol-3-yl)pyridin-3-yl)-3,4-dihydropyrazino[2,3-b]pyrazin-2(1H)-one;
7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;
1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
1-(trans-4-hydroxycyclohexyl)-7-(6-(2-hydroxypropan-2-yl)pyridin-3-yl)-3,4-dihydropyrazino[2,3-b]pyrazin-2(1H)-one;
1-(cis-4-hydroxycyclohexyl)-7-(6-(2-hydroxypropan-2-yl)pyridin-3-yl)-3,4-dihydropyrazino[2,3-b]pyrazin-2(1H)-one;
4-(7-oxo-8-(2-(tetrahydro-2H-pyran-4-yl)ethyl)-5,6,7,8-tetrahydropyrazino[2,3-b]pyrazin-2-yl)benzamide;
7-(1H-indazol-5-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;
1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
7-(1H-indol-5-yl)-1-(2-(tetrahydro-2H-pyran-4-yl)ethyl)-3,4-dihydropyrazino[2,3-b]pyrazin-2(1H)-one;
1-ethyl-7-(2-methyl-6-(4H-1,2,4-triazol-3-yl)pyridin-3-yl)-3,4-dihydropyrazino[2,3-b]pyrazin-2(1H)-one;
7-(1H-indol-6-yl)-1-(2-(tetrahydro-2H-pyran-4-yl)ethyl)-3,4-dihydropyrazino[2,3-b]pyrazin-2(1H)-one;
7-(4-(2-hydroxypropan-2-yl)phenyl)-1-(trans-4-methoxycyclohexyl)-3,4-dihydropyrazino[2,3-b]pyrazin-2(1H)-one;
7-(6-(2-hydroxypropan-2-yl)pyridin-3-yl)-1-(tetrahydro-2H-pyran-4-yl)-3,4-dihydropyrazino[2,3-b]pyrazin-2(1H)-one;
1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((cis-4-methoxycyclohexyl)methyl)-3,4-dihydropyrazino[2,3-b]pyrazin-2(1H)-one;
1-(2-methoxyethyl)-7-(4-methyl-2-(methylamino)-1H-benzo[d]imidazol-6-yl)-3,4-dihydropyrazino[2,3-b]pyrazin-2(1H)-one;
7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;
7-(2-methyl-4-(4H-1,2,4-triazol-3-yl)phenyl)-3,4-dihydropyrazino[2,3-b]pyrazin-2(1H)-one;
1-(2-methoxyethyl)-7-(4-methyl-6-(1H-1,2,4-triazol-3-yl)pyridin-3-yl)-3,4-dihydropyrazino[2,3-b]pyrazin-2(1H)-one;
1-benzyl-7-(2-methyl-4-(4H-1,2,4-triazol-3-yl)phenyl)-3,4-dihydropyrazino[2,3-b]pyrazin-2(1H)-one;
7-(3-fluoro-4-(4H-1,2,4-triazol-3-yl)phenyl)-1-(2-methoxyethyl)-3,4-dihydropyrazino[2,3-b]pyrazin-2(1H)-one;
7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;
1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(trans-4-methoxycyclohexyl)-3,4-dihydropyrazino[2,3-b]pyrazin-2(1H)-one;
7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
1-(2-methoxyethyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((trans-4-methoxycyclohexyl)methyl)-3,4-dihydropyrazino[2,3-b]pyrazin-2(1H)-one;
1-(cyclopentylmethyl)-7-(6-(2-hydroxypropan-2-yl)pyridin-3-yl)-3,4-dihydropyrazino[2,3-b]pyrazin-2(1H)-one;
7-(4-(2-hydroxypropan-2-yl)phenyl)-1-(2-methoxyethyl)-3,4-dihydropyrazino[2,3-b]pyrazin-2(1H)-one;
(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;
7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(4-(trifluoromethyl)benzyl)-3,4-dihydropyrazino[2,3-b]pyrazin-2(1H)-one;
7-(6-(2-hydroxypropan-2-yl)pyridin-3-yl)-1-(3-(trifluoromethyl)benzyl)-3,4-dihydropyrazino[2,3-b]pyrazin-2(1H)-one;
7-(6-(2-hydroxypropan-2-yl)pyridin-3-yl)-1-(3-methoxypropyl)-3,4-dihydropyrazino[2,3-b]pyrazin-2(1H)-one;
7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-methoxyethyl)-3,4-dihydropyrazino[2,3-b]pyrazin-2(1H)-one;
7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;
7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;
7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;

7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;

7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;

7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;

1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; and 1-(2-hydroxyethyl)-7-(2-methyl-6-(1H-1,2,4-triazol-3-yl)pyridin-3-yl)-3,4-dihydropyrazino[2,3-b]pyrazin-2(1H)-one, and pharmaceutically acceptable salts, clathrates, solvates, stereoisomers, tautomers, prodrugs, metabolites and isotopologues thereof.

5.3 Methods for Making Dihydropyrazino-Pyrazine Compounds

The Dihydropyrazino-Pyrazine Compounds can be obtained via standard, well-known synthetic methodology, see e.g., March, J. Advanced Organic Chemistry; Reactions Mechanisms, and Structure, 4th ed., 1992. Starting materials useful for preparing compounds of formula (I) and intermediates therefore, are commercially available or can be prepared from commercially available materials using known synthetic methods and reagents.

Particular methods for preparing compounds of formula (I) are disclosed in U.S. Pat. No. 8,110,578, issued Feb. 7, 2012, and U.S. Pat. No. 8,569,494, issued Oct. 29, 2013, each incorporated by reference herein in their entirety.

5.4 Methods of Use

Provided herein are methods for treating or preventing glioblastoma multiforme (GBM) characterized by MGMT protein expression and/or promoter methylation status, comprising administering an effective amount of a Dihydropyrazino-Pyrazine Compound to a patient having GBM characterized by MGMT protein expression and/or promoter methylation status. In certain embodiments, a Dihydropyrazino-Pyrazine Compound is administered to a patient who has locally advanced, recurrent or metastatic, GBM characterized by MGMT protein expression and/or promoter methylation status, not amenable to curative surgical resection. In another embodiment, a Dihydropyrazino-Pyrazine Compound is administered to a patient having GBM characterized by MGMT protein expression and/or promoter methylation status who has received at least one prior line of chemotherapy, for example, Temozolomide. In some embodiments, a Dihydropyrazino-Pyrazine Compound is administered to a patient who has a GBM characterized by MGMT protein expression and/or promoter methylation status and showing DNA-PK overexpression.

In certain embodiments, a Dihydropyrazino-Pyrazine Compound is administered to a patient having GBM characterized by MGMT protein expression and/or promoter methylation status.

In some such embodiments, the MGMT promoter is hypomethylated. In others, the MGMT protein is expressed.

In certain embodiments, provided herein are methods for achieving a Response Assessment for Neuro-Oncology (RANO) Working Group for glioblastoma multiforme of complete response, partial response or stable disease in a patient having glioblastoma multiforme characterized by MGMT protein expression and/or promoter methylation status, comprising administering an effective amount of a Dihydropyrazino-Pyrazine Compound to said patient.

In one embodiment, provided herein are methods for inhibiting phosphorylation of S6RP, 4E-BP1 and/or AKT in a patient having glioblastoma multiforme characterized by MGMT protein expression and/or promoter methylation status, comprising administering an effective amount of a Dihydropyrazino-Pyrazine Compound to said patient. In some such embodiments, the inhibition of phosphorylation is assessed in a biological sample of the patient, such as in circulating blood and/or tumor cells, skin biopsies and/or tumor biopsies or aspirate. In such embodiments, the amount of inhibition of phosphorylation is assessed by comparison of the amount of phospho-S6RP, 4E-BP1 and/or AKT before and after administration of the Dihydropyrazino-Pyrazine Compound. In certain embodiments, provided herein are methods for measuring inhibition of phosphorylation of S6RP, 4E-BP1 or AKT in a patient having glioblastoma multiforme characterized by MGMT protein expression and/or promoter methylation status, comprising administering an effective amount of a Dihydropyrazino-Pyrazine Compound to said patient, measuring the amount of phosphorylated S6RP, 4E BP1 and/or AKT in said patient, and comparing said amount of phosphorylated S6RP, 4E BP1 and/or AKT to that of said patient prior to administration of an effective amount of a Dihydropyrazino-Pyrazine Compound.

In certain embodiments, provided herein are methods for inhibiting phosphorylation of S6RP, 4E-BP1 and/or AKT in a biological sample of a patient having glioblastoma multiforme characterized by MGMT protein expression and/or promoter methylation status, comprising administering an effective amount of a Dihydropyrazino-Pyrazine Compound to said patient and comparing the amount of phosphorylated S6RP, 4E-BP1 and/or AKT in a biological sample of a patient obtained prior to and after administration of said Dihydropyrazino-Pyrazine Compound, wherein less phosphorylated S6RP, 4E-BP1 and/or AKT in said biological sample obtained after administration of said Dihydropyrazino-Pyrazine Compound relative to the amount of phosphorylated S6RP, 4E-BP1 and/or AKT in said biological sample obtained prior to administration of said Dihydropyrazino-Pyrazine Compound indicates inhibition.

In one embodiment, provided herein are methods for inhibiting DNA-dependent protein kinase (DNA-PK) activity in a patient having glioblastoma multiforme characterized by MGMT protein expression and/or promoter methylation status, comprising administering an effective amount of a Dihydropyrazino-Pyrazine Compound to said patient having GBM characterized by MGMT protein expression and/or promoter methylation status. In some embodiments, DNA-PK inhibition is assessed in the skin of the patient having glioblastoma multiforme characterized by MGMT protein expression and/or promoter methylation status, in one example in a UV light-irradiated skin sample of said patient. In another embodiment, DNA-PK inhibition is assessed in a tumor biopsy or aspirate of a patient having glioblastoma multiforme characterized by MGMT protein expression and/or promoter methylation status. In one embodiment, inhibition is assessed by measuring the amount of phosphorylated DNA-PK S2056 (also known as pDNA-PK S2056) before and after administration of the Dihydropyrazino-Pyrazine Compound. In certain embodiments, provided herein are methods for measuring inhibition of phosphorylation of DNA-PK S2056 in a skin sample of a patient having glioblastoma multiforme characterized by MGMT protein expression and/or promoter methylation status, comprising administering an effective amount of a Dihydropyrazino-Pyrazine Compound to said patient, measuring the amount of phosphorylated DNA-PK S2056 present in the skin sample and comparing said amount of phosphorylated DNA-PK S2056 to that in a skin sample from said patient prior to administration of an effective amount of a Dihydropyrazino-Pyrazine Compound. In one embodiment, the skin sample is irradiated with UV light.

In certain embodiments, provided herein are methods for inhibiting DNA-dependent protein kinase (DNA-PK) activity in a skin sample of a patient having glioblastoma multiforme characterized by MGMT protein expression and/or promoter methylation status, comprising administering an effective amount of a Dihydropyrazino-Pyrazine Compound to said patient and comparing the amount of phosphorylated DNA-PK in a biological sample of a patient obtained prior to and after administration of said Dihydropyrazino-Pyrazine Compound, wherein less phosphorylated DNA-PK in said biological sample obtained after administration of said Dihydropyrazino-Pyrazine Compound relative to the amount of phosphorylated DNA-PK in said biological sample obtained prior to administration of said Dihydropyrazino-Pyrazine Compound indicates inhibition.

In some embodiments, the Dihydropyrazino-Pyrazine Compound is a compound as described herein. In one embodiment, the Dihydropyrazino-Pyrazine Compound is Compound 1 (a Dihydropyrazino-Pyrazine Compound set forth herein having molecular formula $C_{16}H_{16}N_8O$). In one embodiment, the Dihydropyrazino-Pyrazine Compound is Compound 2 (a Dihydropyrazino-Pyrazine Compound set forth herein having molecular formula $C_{21}H_{27}N_5O_3$). In one embodiment, the Dihydropyrazino-Pyrazine Compound is Compound 3 (a Dihydropyrazino-Pyrazine Compound set forth herein having molecular formula $C_{20}H_{25}N_5O_3$). In one embodiment, Compound 1 is 1-ethyl-7-(2-methyl-6-(1H-1,2,4-triazol-3-yl)pyridin-3-yl)-3,4-dihydropyrazino[2,3-b]pyrazin-2(1H)-one, or a tautomer thereof, for example, 1-ethyl-7-(2-methyl-6-(4H-1,2,4-triazol-3-yl)pyridin-3-yl)-3,4-dihydropyrazino[2,3-b]pyrazin-2(1H)-one, or 1-ethyl-7-(2-methyl-6-(1H-1,2,4-triazol-5-yl)pyridin-3-yl)-3,4-dihydropyrazino[2,3-b]pyrazin-2(1H)-one. In one embodiment, Compound 2 is 7-(6-(2-hydroxypropan-2-yl)pyridin-3-yl)-1-((1r,4r)-4-methoxycyclohexyl)-3,4-dihydropyrazino-[2,3-b]pyrazin-2(1H)-one, alternatively named 7-(6-(2-hydroxypropan-2-yl)pyridin-3-yl)-1-((trans)-4-methoxycyclohexyl)-3,4-dihydropyrazino[2,3-b]pyrazin-2(1H)-one, or 7-(6-(2-hydroxypropan-2-yl)pyridin-3-yl)-1-((1R*,4R*)-4-methoxycyclohexyl)-3,4-dihydropyrazino[2,3-b]pyrazin-2(1H)-one. In another embodiment, Compound 3 is 1-((trans)-4-hydroxycyclohexyl)-7-(6-(2-hydroxypropan-2-yl)pyridin-3-yl)-3,4-dihydropyrazino[2,3-b]pyrazin-2(1H)-one, alternatively named 1-((1r,4r)-4-hydroxycyclohexyl)-7-(6-(2-hydroxypropan-2-yl)pyridin-3-yl)-3,4-dihydropyrazino[2,3-b]pyrazin-2(1H)-one. In one embodiment, Compound 3 is a metabolite of Compound 2.

A Dihydropyrazino-Pyrazine Compound can be combined with radiation therapy or surgery. In certain embodiments, a Dihydropyrazino-Pyrazine Compound is administered to patient who is undergoing radiation therapy, has previously undergone radiation therapy or will be undergoing radiation therapy. In certain embodiments, a Dihydropyrazino-Pyrazine Compound is administered to a patient who has undergone GBM removal surgery.

Further provided herein are methods for treating patients who have been previously treated for glioblastoma multiforme characterized by MGMT protein expression and/or promoter methylation status, but are non-responsive to standard therapies, for example with Temozolomide, as well as those who have not previously been treated. Further provided herein are methods for treating patients who have undergone surgery in an attempt to treat the condition at issue, as well as those who have not. Because patients with glioblastoma multiforme characterized by MGMT protein expression and/or promoter methylation status may have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with glioblastoma multiforme characterized by MGMT protein expression and/or promoter methylation status. In some embodiments, the methods described herein additionally comprise administration of Temozolomide. In some such embodiments, the glioblastoma multiforme is Temozolomide resistant.

In one embodiment, the glioblastoma multiforme characterized by MGMT protein expression and/or promoter methylation status is that in which the PI3K/mTOR pathway is activated. In certain embodiments, the glioblastoma multiforme characterized by MGMT protein expression and/or promoter methylation status is that in which the PI3K/mTOR pathway is activated due to ERBB2 mutation, PTEN mutation or loss, NF1 mutation or loss, PIK3Ca mutation, EGFR mutation or overexpression, Met amplification, PDG-FRa activation or amplification, AKT amplification, or a combination thereof. In one embodiment, the EGFR mutation is the EGFRviii mutation.

5.5 Pharmaceutical Compositions and Routes of Administration

Provided herein are compositions, comprising an effective amount of a Dihydropyrazino-Pyrazine Compound, and compositions comprising an effective amount of a Dihydropyrazino-Pyrazine Compound and a pharmaceutically acceptable carrier or vehicle. In some embodiments, the pharmaceutical compositions described herein are suitable for oral, parenteral, mucosal, transdermal or topical administration.

The Dihydropyrazino-Pyrazine Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Dihydropyrazino-Pyrazine Compound in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a Dihydropyrazino-Pyrazine Compound to be administered to a patient is rather widely variable and can be subject to the judgment of a health-care practitioner. In general, the Dihydropyrazino-Pyrazine Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight, about 0.25 mg/kg of a patient's body weight to about 0.5 mg/kg of a patient's body weight, or about 0.007 mg/kg of a patient's body weight to about 1.7 mg/kg of patient's body weight. In one embodiment, one dose is given per day. In another embodiment, two doses are given per day. In any given case, the amount of the Dihydropyrazino-Pyrazine Compound administered will depend on such factors as the solubility of the active component, the formulation used and the route of administration.

In another embodiment, provided herein are methods for the treatment or prevention of glioblastoma multiforme characterized by MGMT protein expression and/or promoter methylation status, comprising the administration of about 0.375 mg/day to about 750 mg/day, about 0.75 mg/day to about 375 mg/day, about 3.75 mg/day to about 75 mg/day, about 7.5 mg/day to about 55 mg/day, about 18 mg/day to about 37 mg/day, about 0.5 mg/day to about 60 mg/day, or about 0.5 mg/day to about 128 mg/day of a Dihydropyrazino-Pyrazine Compound to a patient in need thereof. In another embodiment, provided herein are methods for the treatment or prevention of glioblastoma multiforme characterized by MGMT protein expression and/or promoter methylation status, comprising the administration of about 0.5 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Dihydropyrazino-Pyrazine Compound to a patient in need thereof. In a particular embodiment, the methods disclosed herein comprise the administration of 0.5 mg/day, 1 mg/day, 2 mg/day, 4 mg/day, 8 mg/day, 10 mg/day, 15 mg/day, 16 mg/day, 20 mg/day, 25 mg/day, 30 mg/day, 45 mg/day, 60 mg/day, 90 mg/day, 120 mg/day or 128 mg/day of a Dihydropyrazino-Pyrazine Compound to a patient in need thereof.

In another embodiment, provided herein are unit dosage formulations that comprise between about 0.1 mg and about 2000 mg, about 1 mg and 200 mg, about 35 mg and about 1400 mg, about 125 mg and about 1000 mg, about 250 mg and about 1000 mg, or about 500 mg and about 1000 mg of a Dihydropyrazino-Pyrazine Compound.

In a particular embodiment, provided herein are unit dosage formulation comprising about 0.1 mg, 0.25 mg, 0.5 mg, 1 mg, 2.5 mg, 5 mg, 7.5 mg, 10 mg, 15 mg, 20 mg, 30 mg, 35 mg, 45 mg, 50 mg, 60 mg, 70 mg, 75 mg, 100 mg, 125 mg, 140 mg, 150 mg, 175 mg, 200 mg, 250 mg, 280 mg, 300 mg, 350 mg, 400 mg, 500 mg, 560 mg, 600 mg, 700 mg, 750 mg, 800 mg, 1000 mg or 1400 mg of a Dihydropyrazino-Pyrazine Compound. In a particular embodiment, provided herein are unit dosage formulations that comprise 2.5 mg, 5 mg, 7.5 mg, 8 mg, 10 mg, 15 mg, 20 mg, 30 mg, 45 mg, 50 mg, 60 mg or 100 mg of a Dihydropyrazino-Pyrazine Compound. In a particular embodiment, provided herein are unit dosage formulations that comprise 5 mg, 7.5 mg or 10 mg of a Dihydropyrazino-Pyrazine Compound.

A Dihydropyrazino-Pyrazine Compound can be administered once, twice, three, four or more times daily.

In certain embodiments, a Dihydropyrazino-Pyrazine Compound is administered to a patient in cycles. Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a Dihydropyrazino-Pyrazine Compound is administered daily in single or divided doses for about 3 days, about 5 days, about one week, about two weeks, about three weeks, about four weeks (e.g., 28 days), about five weeks, about six weeks, about seven weeks, about eight weeks, about ten weeks, about fifteen weeks, or about twenty weeks, followed by a rest period of about 1 day to about ten weeks. In one embodiment, the methods provided herein contemplate cycling treatments of about one week, about two weeks, about three weeks, about four weeks, about five weeks, about six weeks, about eight weeks, about ten weeks, about fifteen weeks, or about twenty weeks. In some embodiments, a Dihydropyrazino-Pyrazine Compound is administered in single or divided doses for about 3 days, about 5 days, about one week, about two weeks, about three weeks, about four weeks (e.g., 28 days), about five weeks, or about six weeks with a rest period of about 1, 2, 3, 4, 5, 6, 7, 8, 9, 10, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

A Dihydropyrazino-Pyrazine Compound can be administered orally for reasons of convenience. In one embodiment, when administered orally, a Dihydropyrazino-Pyrazine Compound is administered with a meal and water. In another embodiment, the Dihydropyrazino-Pyrazine Compound is dispersed in water or juice (e.g., apple juice or orange juice) and administered orally as a suspension. In another embodiment, when administered orally, a Dihydropyrazino-Pyrazine Compound is administered in a fasted state.

The Dihydropyrazino-Pyrazine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Dihydropyrazino-Pyrazine Compound without an additional carrier, excipient or vehicle.

In another embodiment, provided herein are compositions, comprising an effective amount of a Dihydropyrazino-Pyrazine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Dihydropyrazino-Pyrazine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Dihydropyrazino-Pyrazine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Dihydropyrazino-Pyrazine Compound can be delayed or prolonged by proper formulation. For example, a slowly soluble pellet of the Dihydropyrazino-Pyrazine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Dihydropyrazino-Pyrazine Compound in oily or emulsified vehicles that allow it to disperse slowly in the serum.

In certain embodiments, Compound 2 is administered in a formulation set forth in U.S. Patent Application Publication No. 2013-0142873, published Jun. 6, 2013, which is incorporated herein in its entirety (see particularly paragraph [0323] to paragraph [0424], and paragraph [0636] to paragraph [0655]). In other embodiments, Compound 2 is administered in a formulation set forth in U.S. Provisional Patent Application No. 61/828,506, filed May 29, 2013, which is incorporated herein in its entirety (see particularly paragraph [0246] to paragraph [0403], and paragraph [0571] to paragraph [0586]).

In certain embodiments, the Compound 1 is administered in a formulation set forth in U.S. Provisional Application No. 61/813,064, filed Apr. 17, 2013, which is incorporated herein in its entirety (see particularly paragraph [0168] to paragraph [0189] and paragraph [0262] to paragraph [0294]). In other embodiments, Compound 1 is administered in a formulation set forth in U.S. Provisional Patent Application No. 61/911,201, filed Dec. 3, 2013, which is incorporated herein in its entirety (see particularly paragraph [0170] to paragraph [0190], and paragraph [0264] to paragraph [0296]).

5.6 Kits

In certain embodiments, provided herein are kits comprising a Dihydropyrazino-Pyrazine Compound.

In other embodiments, provide herein are kits comprising a Dihydropyrazino-Pyrazine Compound and means for monitoring patient response to administration of said Dihydropyrazino-Pyrazine Compound. In certain embodiments, the patient has glioblastoma multiforme characterized by MGMT protein expression and/or promoter methylation status. In particular embodiments, the patient response measured is inhibition of disease progression, inhibition of tumor growth, reduction of primary and/or secondary tumor(s), relief of tumor-related symptoms, improvement in quality of life, delayed appearance of primary and/or secondary tumors, slowed development of primary and/or secondary tumors, decreased occurrence of primary and/or secondary tumors, slowed or decreased severity of secondary effects of disease, arrested tumor growth or regression of tumor.

In other embodiments, provided herein are kits comprising a Dihydropyrazino-Pyrazine Compound and means for measuring the amount of inhibition of phosphorylation of S6RP, 4E-BP1 and/or AKT in a patient. In certain embodiments, the kits comprise means for measuring inhibition of phosphorylation of S6RP, 4E-BP1 and/or AKT in circulating blood or tumor cells and/or skin biopsies or tumor biopsies/aspirates of a patient. In certain embodiments, provided herein are kits comprising a Dihydropyrazino-Pyrazine Compound and means for measuring the amount of inhibition of phosphorylation as assessed by comparison of the amount of phospho-S6RP, 4E-BP1 and/or AKT before, during and/or after administration of the Dihydropyrazino-Pyrazine Compound. In certain embodiments, the patient has glioblastoma multiforme characterized by MGMT protein expression and/or promoter methylation status.

In other embodiments, provided herein are kits comprising a Dihydropyrazino-Pyrazine Compound and means for measuring the amount of inhibition of DNA-dependent protein kinase (DNA-PK) activity in a patient. In certain embodiments, the kits comprise means for measuring the amount of inhibition of DNA-dependent protein kinase (DNA-PK) activity in a skin sample and/or a tumor biopsy/aspirate of a patient. In one embodiment, the kits comprise a means for measuring the amount of pDNA-PK S2056 in a skin sample and/or a tumor biopsy/aspirate of a patient. In one embodiment, the skin sample is irradiated by UV light. In certain embodiments, provided herein are kits comprising a Dihydropyrazino-Pyrazine Compound and means for measuring the amount of inhibition of DNA-dependent protein kinase (DNA-PK) activity before, during and/or after administration of the Dihydropyrazino-Pyrazine Compound. In certain embodiments, provided herein are kits comprising a Dihydropyrazino-Pyrazine Compound and means for measuring the amount of phosphorylated DNA-PK S2056 before, during and/or after administration of the Dihydropyrazino-Pyrazine Compound. In certain embodiments, the patient has glioblastoma multiforme characterized by MGMT protein expression and/or promoter methylation status.

In certain embodiments, the kits provided herein comprise an amount of a Dihydropyrazino-Pyrazine Compound effective for treating or preventing glioblastoma multiforme characterized by MGMT protein expression and/or promoter methylation status. In certain embodiments, the kits provided herein comprise Compound 1.

In certain embodiments, the kits provided herein further comprise instructions for use, such as for administering a Dihydropyrazino-Pyrazine Compound and/or monitoring patient response to administration of a Dihydropyrazino-Pyrazine Compound.

6. EXAMPLES

6.1 Compound Formulations

Illustrative formulations of Compound 1 useful in the methods provided herein are set forth in Table 1, below.

TABLE 1

Exemplary Tablet Formulations

| Ingredients | % w/w (mg) Batch # | | | |
|---|---|---|---|---|
| | 1 | 2 | 3 | 4 |
| Compound 1 (active ingredient) | 10 | 10 | 10 | 10 |
| Mannitol (Mannogem EZ) | qs | qs | qs | qs |
| Microcrystalline Cellulose (PH 112) | 25 | 25 | 25 | 25 |
| Sodium Starch Glycolate | 3 | 3 | 3 | 3 |
| Silicon dioxide | 1 | 1 | 1 | 1 |
| Stearic acid | 0.5 | 0.5 | 0.5 | 0.5 |
| Disodium EDTA | | | 0.5 | 0.5 |
| BHT | | 0.4 | | 0.4 |
| Magnesium Stearate | 0.65 | 0.65 | 0.65 | 0.65 |
| Total | 100 | 100 | 100 | 100 |
| Color | Yellow | Yellow | Yellow | Yellow |

Illustrative formulations of Compound 2 useful in the methods provided herein are set forth in Tables 2-5, below.

TABLE 2

| Ingredients | Amounts | |
|---|---|---|
| | mg | % w/w |
| Compound 2 | 20.0 | 15.38 |
| Lactose monohydrate, NF (Fast Flo 316) | 63.98 | 49.22 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry yellow 03K12429 | 5.2 | 4.0 |

TABLE 3

| Ingredients | Amounts | |
|---|---|---|
| | mg | % w/w |
| Compound 2 | 5.0 | 3.80 |
| Lactose monohydrate, NF (Fast Flo 316) | 78.98 | 60.70 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry II pink 85F94211 | 5.2 | 4% weight gain |

TABLE 4

| Ingredients | Amounts | | | |
|---|---|---|---|---|
| | mg | | | % w/w |
| Compound 2 | 15.0 | 20.0 | 30.0 | 15.38 |
| Lactose monohydrate, NF (Fast Flo 316) | 48.37 | 64.50 | 96.75 | 49.62 |
| Microcrystalline cellulose, NF (Avicel pH 112) | 30.23 | 40.30 | 60.45 | 31.00 |
| Croscarmellose sodium, NF (Ac-Di-Sol) | 2.925 | 3.90 | 5.85 | 3.00 |
| Magnesium Stearate, NF | 0.975 | 1.30 | 1.95 | 1.00 |
| Total | 97.50 | 130.0 | 195.00 | 100 |
| Opadry yellow 03K12429 | 3.9 | | | 4.0 |
| Opadry II Pink 85F94211 | | 5.2 | | 4.0 |
| Opadry Pink 03K140004 | | | 7.8 | 4.0 |

TABLE 5

| Ingredients | Amounts | |
|---|---|---|
| | mg | % w/w |
| Compound 2 | 45.00 | 15.38 |
| Lactose monohydrate, NF (Fast Flo 316) | 143.955 | 49.22 |
| Microcrystalline cellulose, NF (Avicel pH 102) | 90.675 | 31.00 |
| Croscarmellose sodium, NF (Ac-Di-Sol) | 8.775 | 3.00 |
| Stearic acid, NF | 1.170 | 0.40 |
| Magnesium Stearate, NF | 2.925 | 1.00 |
| Total | 292.50 | 100 |
| Opadry pink 03K140004 | 11.70 | 4.0 |

6.2 Biological Examples

6.2.1 Biochemical Assays mTOR HTR-FRET Assay. The following is an example of an assay that can be used to determine the TOR kinase inhibitory activity of a test compound. Dihydropyrazino-Pyrazine Compounds were dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen mTOR (cat#PV4753) was diluted in this buffer to an assay concentration of 0.200 µg/mL.

ATP/Substrate solution: 0.075 mM ATP, 12.5 mM $MnCl_2$, 50 mM Hepes, pH 7.4, 50 mM β-GOP, 250 nM Microcystin LR, 0.25 mM EDTA, 5 mM DTT, and 3.5 µg/mL GST-p70S6.

Detection reagent solution: 50 mM HEPES, pH 7.4, 0.01% Triton X-100, 0.01% BSA, 0.1 mM EDTA, 12.7 µg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 µL of the Simple mTOR buffer is added 0.5 µL of test compound in DMSO. To initiate the reaction 5 µL of ATP/Substrate solution was added to 20 µL of the Simple TOR buffer solution (control) and to the compound solution prepared above. The assay was stopped after 60 min by adding 5 µL of a 60 mM EDTA solution; 10 µL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

Dihydropyrazino-Pyrazine Compounds were tested in the mTOR HTR-FRET assay and were found to have activity therein, with certain compounds having an $IC_{50}$ below 10 µM in the assay, with some compounds having an $IC_{50}$ between and 0.005 nM and 250 nM, others having an $IC_{50}$ between 250 nM and 500 nM, others having an $IC_{50}$ between 500 nM and 1 µM, and others having an $IC_{50}$ between 1 µM and 10 µM.

DNA-PK Assay. DNA-PK assay is performed using the procedures supplied in the Promega DNA-PK assay kit (catalog #V7870). DNA-PK enzyme can be purchased from Promega (Promega cat#V5811).

Selected Dihydropyrazino-Pyrazine Compounds as described herein have, or are expected to have, an $IC_{50}$ below 10 µM in this assay, with some Dihydropyrazino-Pyrazine Compounds as described herein having an $IC_{50}$ below 1 µM, and others having an $IC_{50}$ below 0.10 µM.

6.2.2 Cell Based Assays

Growth Inhibition Assay for Glioblastoma Multiforme (GBM) Characterized by MGMT Protein Expression and/or Promoter Methylation Status. A compound can be tested as follows: A test compound (a Dihydropyrazino-Pyrazine Compound set forth herein) is dissolved in dimethyl sulfoxide (DMSO) to prepare a 10 mM stock solution. A serial titration is performed to produce a working concentration range of 1.5 µM to 10 mM. Aliquots to produce final concentrations of 1.5 nM to 10 µM are spotted via an acoustic dispenser (EDC ATS-100) into an empty 384-well plate. The test compound is spotted in a 10-point serial dilution fashion (3-fold dilution) in duplicate within the plate. The DMSO concentration is kept constant for a final assay concentration of 0.1% DMSO. Plates are replicated for use with different GBM cells (for example GBM cell lines or patient derived samples) and testing periods. After compound plate replication, all plates are sealed (Agilent ThermoLoc) and stored at −20° C. for up to 1 month. When ready for testing, plates are removed from the freezer, thawed, and unsealed just prior to the addition of the test cells. Prior to testing, cells are grown and expanded in culture flasks to provide sufficient amounts of starting material. Cells are then diluted to the appropriate densities and added directly to the test-compound-spotted 384-well plates. Cells are allowed to grow for 72 hours at 37° C./5% $CO_2$. At the time when test compounds are added ($t_0$), initial cell numbers are assessed via a viability assay (Cell Titer-Glo) by quantifying the level of luminescence generated by ATP present in viable cells. After 72 hours, cell viability of test-compound-treated cells is assessed via Cell Titer-Glo and luminescence measurement. Cell lines are assayed for growth inhibition by the test compound in at least 3 independent tests. A control cell line is included in each of the assays. The test compound response against this control cell line is monitored closely to enable comparison of the data generated through the assay period. All data are normalized and presented as a percentage of the DMSO-treated cells. Results are then expressed as a $GI_{50}$ value. The $GI_{50}$ value corrects for the cell count at time zero. The MGMT promoter methylation status is determined by, for example, methylation-specific PCR (MSP) and bisulfite sequencing (BiSEQ) of 24 neighboring CpG sites. Additionally, the MGMT protein expression can be determined by, for example immunohistochemistry or Western Blot.

In one embodiment, the Dihydropyrazino-Pyrazine Compounds show growth inhibition of GBM cells characterized by hypomethylation of the MGMT promoter. In another embodiment, the Dihydropyrazino-Pyrazine Compound show growth inhibition of GBM cells characterized by MGMT protein expression.

Apoptosis Assay for GBM Cells Characterized by MGMT Protein Expression and/or Promoter Methylation Status. Prior to testing, GBM cells are grown and expanded in culture flasks to provide sufficient amounts of starting material. Cells are then diluted to their desired densities and added directly to test-compound-spotted 384-well plates. Cells are allowed to grow for 24 hours in 5% $CO_2$ at 37° C. The apoptotic response is assessed by quantifying the activities of caspase 3 and caspase 7 (Caspase 3/7-Glo) in treated cells and control cells at the 24-hour time point. All data is normalized and represented as a value relative to the DMSO-treated cells. Results are then expressed as CalX, which is the minimum test compound concentration required to double the levels of caspase 3/7 relative to those of the DMSO-treated cells during their treatment period.

The MGMT promoter methylation status is determined by, for example, methylation-specific PCR (MSP) and bisulfite sequencing (BiSEQ) of 24 neighboring CpG sites. Additionally, the MGMT protein expression is determined by, for example immunohistochemistry or Western Blot.

In one embodiment, the Dihydropyrazino-Pyrazine Compounds show apoptosis of GBM cells characterized by hypomethylation of the MGMT promoter. In another embodiment, the Dihydropyrazino-Pyrazine Compounds show apotosis of GBM cells characterized by MGMT protein expression.

Gliomasphere Cell Number Assay. Primary patient-derived GBM tumor samples were dissociated and plated under culture conditions that produce gliomaspheres (i.e. DMEM/F12 medium supplemented with B27, 20 ng/mL bFGF, 50 ng/mL EGF, penicillin/streptomycin, L-glutamine and 5 ug/mL heparin). Cells were plated at a density of 5000 cells/well and allowed to acclimate overnight at 37° C. The Dihydropyrazino-Pyrazine Compounds were added to the cultures on Day 2 and cells were kept in culture until Day 9. On Day 9, the cells were fixed with PFA/methanol and the next day assessed for cell number, using for example, SYTO-9 fluorescent DNA dye. Plates were read 48 h later with a laser scanning imager. Results for Compound 1 are shown in Table 6. $IC_{50}$ values represent 50% cell numbers compared to the DMSO control. As can be seen from Table 6, Compound 1 showed activity on GBM cells that had MGMT protein expression and GBM cells that had hypomethylated MGMT promoter.

TABLE 6

Compound 1 and Compound 2 treatment effect on cell number

| Cell Line | Diagnosis | EGFR Ampl | EGFR viii | PTEN status (Tumor) | PTEN Status (Cell line) | MGMT Methylation or espression status | Cmpd 1 ($IC_{50}$-nM) Cell Survival | Cmpd 2 ($IC_{50}$-nM) Cell Survival |
|---|---|---|---|---|---|---|---|---|
| 248 | Recurrent | | − | + | + | Slightly elevated | 441.3 | |
| 371 | Recurrent | + | − | +/− | + | − | 367.8 | |
| 301 | Primary | + | | | − | − | 312.6 | |
| 336 | Recurrent | | | | + | + | 231.3 | 866.4 |
| 393 | Primary | | − | | | + | 178.2 | |
| 206 | Recurrent | | | − | + | Unkn/Highly Expressed | 163 | 117.6 |
| 347 | Recurrent | + | | +/− | − | − | 162.9 | 172.6 |
| 229 | Recurrent | | | | − | | 115.4 | |
| 277 | Secondary/Recurrent | | | | + | | 107.1 | 106.5 |
| 207 | Recurrent | | | | + | | 100 | |
| 254 | Recurrent | | | | + | | 99.6 | 215.7 |
| 350 | Recurrent | | | | − | | 99.6 | |
| 378 | Recurrent | + | | | | − | 81.3 | 156.5 |
| 296 | Recurrent | + | | | − | − | 74.5 | 257.0 |
| 250 | Recurrent | − | | − | − | Unkn/Highly Expressed | 70.6 | 50.7 |
| 217 | Primary | | | | − | − | 71.9 | 96.3 |
| 245 | Recurrent | + | | + | + | | 68.7 | |
| 308 | Recurrent | − | | − | + | Unkn/Highly Expressed | 68.2 | |
| 390 | Primary | − | − | − | + | − | 65.9 | |
| 157 | Primary | | | | + | − | 46.8 | 170.7 |
| 374 | Primary | | + | | − | | 165.0 | |

Unkn: Unknown

Gliomasphere Formation Assay. Primary patient-derived GBM tumor samples were dissociated and plated under culture conditions (i.e. DMEM/F12 medium supplemented with B27, 20 ng/mL bFGF, 50 ng/mL EGF, penicillin/streptomycin, L-glutamine and 5 ug/mL heparin) that produce gliomaspheres. Cells were plated at a density of 50 cells per well and allowed to acclimate overnight at 37° C. The Dihydropyrazino-Pyrazine Compounds were added to the cultures on Day 2 and replenished every 7 days. EGF and FGF were also replenished every 7 days. The cells were fixed with PFA/methanol when the smallest sphere was greater than 60 microns, typically 3-5 weeks. The cells were fixed with PFA/methanol and the next day assessed for cell number, using for example, SYTO-9 fluorescent DNA dye. Plates were read 48 h later with a laser scanning imager. $IC_{50}$ values represent 50% sphere formation compared to the DMSO control. As can be seen from Table 7, Compound 1 showed activity on GBM cells that had MGMT protein expression.

various doses of Compound 1 pre-treatment were not significantly different from the number of spheres formed by the control untreated cells suggesting the percentage of sphere-initiating cells in the total cell population of the patient-derived GBM cell lines was not altered by Compound 1 treatment. Compound 1 may target both the sphere-initiating cells as well as the more committed progenitor cells thus the percentage of sphere-initiating cells in the culture remains constant after Compound 1 treatment. No tumorspheres re-formed after cell line 254 was treated with 500 nM of Compound 1 suggesting 500 nM of Compound 1 is cytotoxic to the sphere-initiating cells of cell line 254. Cell line 282 was not tested at the 100 nM or 500 nM concentrations of Compound 1.

Combination Effect of Compound 1 and Temezolomide (TMZ) on TMZ Resistant and TMZ Sensitive Patient-Derived GBM Cell Lines. TMZ is an alkylating agent that delivers a methyl group to the purine bases of DNA ($O^6$-guanine; $N^7$-guanine and $N^3$-adenine). The cytotoxic lesion,

TABLE 7

Sphere forming capacity in the presence of Compound 1 and Compound 2.

| Cell Line | Diagnosis | EGFR Ampl | EGFR viii | PTEN status (Tumor) | PTEN Status (Cell line) | MGMT Methylation or espression status | Cmpd 1 ($IC_{50}$-nM) Sphere formation | Cmpd 2 ($IC_{50}$-nM) Sphere formation |
|---|---|---|---|---|---|---|---|---|
| 248 | Recurrent | | − | + | + | Slightly elevated | | |
| 371 | Recurrent | + | − | +/− | + | − | | |
| 301 | Primary | + | | − | − | | | |
| 336 | Recurrent | | | | + | + | | |
| 393 | Primary | − | | | | + | | |
| 206 | Recurrent | | | − | + | Unkn/Highly Expressed | 142.4 | |
| 347 | Recurrent | + | | +/− | − | − | | |
| 229 | Recurrent | | | | − | | | |
| 277 | Secondary/Recurrent | | | | + | | | |
| 207 | Recurrent | | | | + | | | |
| 254 | Recurrent | | | | + | | | |
| 350 | Recurrent | | | | − | − | 39.3 | 243.5 |
| 378 | Recurrent | + | | | − | − | | |
| 296 | Recurrent | + | | | − | − | 544.3 | 1700 |
| 250 | Recurrent | − | | − | − | Unkn/Highly Expressed | 39.6 | |
| 217 | Primary | | | − | − | | 42.1 | 68.9 |
| 245 | Recurrent | + | | + | + | | 22.6 | 65.1 |
| 308 | Recurrent | − | | − | + | Unkn/Highly Expressed | | 76.7 |
| 390 | Primary | − | − | − | + | − | | |
| 157 | Primary | | | | + | − | | |
| 309 | Recurrent | | | | | ND | 159.3 | |
| 282 | Primary | | | | | ND | 25.8 | |

Unkn: Unknown

Sphere-Reformation Assay. Patient-derived GBM cell lines cultured under tumorsphere culture conditions maintain a highly heterogenous population of cells, including both sphere-initiating cells, as well as more committed progenitor cells with limited proliferative capabilities. To determine if Compound 1 specifically targets the sphere-initiating cell population, we performed a sphere re-formation assay after Compound 1 pre-treatment. 500,000 cells/10 mL of tumorsphere media were treated with the indicated dose of Compound 1 for 7 days. Cells that survived the 7 day treatment were washed free of Compound 1, dissociated into single cells, and plated at clonal density for the sphere formation assay without Compound 1. FIG. 1 demonstrates that for patient-derived GBM cell lines 206, 217, 254, and 282, the number of spheres formed by cells that survived $O^6$-methylguanine ($O^6$-MeG), caused by TMZ can be directly removed by methylguanine methyltransferase (MGMT) via direct repair and can also activate mechanisms of mismatch repair (MMR). Futile cycles of MMR lead to the formation of double-stranded DNA breaks and activation of the DNA-PK mediated mechanisms of double-stranded break repair. Because Compound 1 inhibits mTORC1 and mTORC2, components of the PI3Kinase signaling pathway, as well as DNA-PK, an enzyme that mediates the NHEJ pathway of double-stranded DNA repair the combined treatment with Compound 1 and TMZ was tested for enhanced TMZ killing of patient-derived GBM cell lines.

Tumorspheres grown under tumorsphere culture conditions were harvested, dissociated into single cells, and plated at 5,000 cells/well in 96-well plates. TMZ and Compound 1 were dosed concurrently and 12 wells per dose combination were treated for 7 days prior to cell counting. When the value of the column % actual inhibition divided by % inhibition calculated based on summation is >1=synergism, ~1=summation, <1=antagonism.

TABLE 7

Fractional product calculations for concomitant combinations of TMZ and Compound 1 on patient-derived GBM cell line 206.

| TMZ [µM] | Cmpd 1 [nM] | % Actual inh. | % Inh. calc. from summation | % Actual Inh/% Inh. calc. from summation |
|---|---|---|---|---|
| 25 | | 11.4% | | |
| 50 | | 0.0% | | |
| 100 | | 0.0% | | |
| 200 | | 4.3% | | |
| | 50 | 10.6% | | |
| | 100 | 23.1% | | |
| | 500 | 65.8% | | |
| 25 | 50 | 46.0% | 20.8% | 2.21 |
| 25 | 100 | 41.1% | 31.9% | 1.29 |
| 25 | 500 | 68.5% | 69.7% | 0.98 |
| 50 | 50 | 23.7% | 10.6% | 2.24 |
| 50 | 100 | 35.9% | 23.1% | 1.55 |
| 50 | 500 | 68.4% | 65.8% | 1.04 |

Cell line 206, which expresses high mRNA levels of MGMT, is TMZ resistant as evidenced by the minimal inhibitory effect of 50, 100, and 200 µM of TMZ on cell survival (Table 8). Concomitant treatment of TMZ, at 25 µM or 50 µM, with a low dose of Compound 1, e.g. 50 nM, synergistically inhibited GBM cell survival. At higher doses of Compound 1, concomitant Compound 1 and TMZ treatment resulted in additive effects (Table 8). This result suggests that Compound 1 in combination with TMZ has synergistic effects on TMZ resistant GBM, which may be dose dependent.

TABLE 8

Fractional product calculations for concomitant combinations of TMZ and Compound 1 on patient-derived GBM cell line 217.

| TMZ [µM] | Cmpd 1 [nM] | % Actual inh. | % Inh. calc. from summation | % Actual Inh/% Inh. calc. from summation |
|---|---|---|---|---|
| 25 | | 69.0% | | |
| 50 | | 73.0% | | |
| 100 | | 77.0% | | |
| | 100 | 51.0% | | |
| 25 | 100 | 78.4% | 85.1% | 0.92 |
| 50 | 100 | 80.4% | 87.1% | 0.92 |
| 100 | 100 | 83.7% | 88.7% | 0.94 |

The effect of combined Compound 1 and TMZ treatment was also tested on a TMZ sensitive cell line 217. TMZ treatment at 25, 50, and 100 µM inhibited cell survival by 69%, 73%, and 77% respectively (Table 9) demonstrating that line 217 is a TMZ sensitive line. For line 217, concurrent treatment with different dose combinations of Compound 1 and TMZ resulted in an additive effect (Table 9) suggesting that Compound 1 neither enhances nor antagonizes TMZ induced cell killing in a TMZ sensitive cell line.

6.2.3 In Vivo Assays

Xenograft studies are conducted with GBM characterized by MGMT protein expression and/or promoter methylation status and/or expression status tumor-bearing mice. SCID or nude mice are inoculated subcutaneously with GBM cells characterized by MGMT protein expression and/or promoter methylation status and expression status in the flank region above the right hind leg. Following inoculation of the animals, the tumors are allowed to grow to about 150-200 mm$^3$ prior to randomization. A test compound is formulated in 0.5% CMC and 0.25% Tween 80 in water (as a suspension). The animals are orally administered vehicle (CMC-Tween) or a test compound once daily (QD) for 26-40 days. Doses of a test compound can range between 1 and 5 mg/kg. Tumors are measured twice a week using calipers and tumor volumes are calculated using the formula of $W^2 \times L/2$ (wherein "W" is tumor width and "L" is tumor length).

Compound 1 and Compound 2 Efficacy Studies in Patient-Derived Glioblastoma Neurospheres and Xenograft Tumors. Immunocompromised mice (nude mouse NCRNU-M, TACONIC) were implanted with a GBM neurosphere line derived from fresh surgical specimens. The cell line was characterized as following:

| GBM Neurosphere | Classification | Mgmt Status | Known Mutations |
|---|---|---|---|
| HF2354 | Primary GBM, Gliadel treated | — | TP53 V216L |

Patient derived xenograft (PDX) treatments started four weeks prior to when the first animal was expected to become symptomatic. Compound 1 or Compound 2 were administered at 5 mg/kg and 10 mg/kg dosage, respectively, by oral gavage once a day, Monday through Friday. Control animals were administered vehicle alone. Target hit cohorts were treated with one dose of each compound and sacrificed 2 and 24 h later (n=3/group). As necessary, fluids and supplemental food were administered to ameliorate weight loss.

Results: Compound 1 monotherapy significantly increased survival of HF2354 PDX. No effect in survival was observed for Compound 2. (see FIG. 2)

6.2.4 Clinical Study

Phase 1B, Multi-Center, Open-Label, Dose Finding Study to Assess the Safety, Tolerability, Pharmacokinetics and Preliminary Efficacy of Compound 1 Administered Orally to Subjects with GBM Characterized by MGMT Protein Expression and/or Promoter Methylation Status Study Objectives.

The primary objectives of the study are to determine: (1) the safety and tolerability of Compound 1; (2) the non-tolerated dose (NTD) of Compound 1; (3) the maximum tolerated dose (MTD) of Compound 1; and (4) the pharmacokinetics (PK) of Compound 1, when Compound 1 is administered orally to patients having GBM characterized by MGMT protein expression and/or promoter methylation status.

The secondary objectives of the study are to: (1) evaluate the extent of inhibition of phosphorylation of S6RP and/or 4E-BP1 for mTORC1 activity and AKT and/or other relevant biomarkers for mTORC2 activity in blood, skin and/or tumor biopsies/aspirates, when available before and during treatment with Compound 1; (2) evaluate the inhibition of DNA-dependent protein kinase (DNA-PK) activity in skin samples irradiated by UV light, and/or tumor biopsies/aspirates using pDNA-PK S2056 and/or other relevant biomarkers for DNA damage pathways before and during Compound 1 treatment; and (3) evaluate the efficacy of Compound 1.

The exploratory objectives of the study are to: (1) evaluate glucose homeostasis during Compound 1 treatment; (2) explore the relationship between Compound 1 exposure in blood and tumor with response (inhibition of mTOR and DNA-PK biomarkers); (3) explore the relationship between Compound 1 exposure in blood and tumor with clinical outcomes and adverse events (AEs); (4) explore the effect of Compound 1 on biomarkers, including apoptosis and/or inhibition of proliferation, in pre- and during-treatment tumor biopsies, when available; (5) investigate whether responses to Compound 1 could be explained by differences in protein expression or genetic variation including, but not limited to, investigation of components of the PI3K/AKT/mTOR pathway, DNA damage response pathways, and the p53 family of genes; (6) identify the principal metabolites of Compound 1 in plasma and urine; and (7) analyze recovered CTC for molecular abnormalities and changes in mTOR and DNA-PK biomarkers.

Study Design.

In this study, Compound 1 is administered orally to patients having GBM characterized by MGMT protein expression and/or promoter methylation status.

Subjects will start Compound 1 at 10 mg BID. Subjects will be evaluated for safety and antitumor activity after every two/three cycles of therapy.

Study Population.

Men and women, 18 years or older, with GBM characterized by MGMT protein expression and/or promoter methylation status, and including subjects who have progressed on (or not been able to tolerate) standard anticancer therapy, or for whom no other approved therapy exists.

Inclusion Criteria.

Inclusion criteria are: (1) understand and voluntarily sign an informed consent document before any study-related assessments/procedures are conducted; (2) men and women, 18 years or older, with histological or cytological confirmation of GBM characterized by MGMT protein expression and/or promoter methylation status; (3) consent to screening tumor biopsy; (4) ECOG PS of 0 or 1; (5) the following laboratory values: (i) absolute neutrophil count (ANC)≥1.5×109/L; (ii) hemoglobin (Hgb)≥9 g/dl; (iii) platelets (plt) ≥100×109/L; (iv) potassium within normal range, or correctable with supplements; (v) AST/SGOT and ALT/SGPT≤2.5×Upper Limit of Normal (ULN) or ≤5.0×ULN if liver tumor is present; (vi) serum total bilirubin≤1.5×ULN; (vii) serum creatinine≤1.5×ULN, or 24-hr clearance≥50 mL/min; and (viii) negative serum or urine pregnancy test within 72 hrs before starting study treatment in females of childbearing potential; (6) able to adhere to the study visit schedule and other protocol requirements; (7) subject consent to retrieve formalin-fixed, paraffin-embedded (FFPE) archival tumor tissue, either in tumor blocks or sectioned/mounted specimens; (8) histologically-confirmed GBM characterized by MGMT protein expression and/or promoter methylation status; (9) has received prior treatment including radiation and/or chemotherapy, with radiation completed >12 weeks prior to Day 1; (10) planned salvage surgical tumor resection on Day 15±7 days, anticipated to yield ≥300 mg tumor tissue. Screening tumor biopsy is not required; (11) no prior or scheduled Gliadel® wafer implant unless area of assessment and planned resection is outside the region previously implanted; (12) no prior interstitial brachytherapy or stereotactic radiosurgery unless area of assessment and planned resection is outside the region previously treated; (13) no enzyme-inducing anti-epileptic drugs (EIAED) such as carbamazepine, phenyloin, phenobarbital, or primidone within 14 days before Day 1; (14) able to undergo repeated magnetic resonance imaging (MRI) scans. Cohort may be expanded to enroll a minimum of 5 subjects with tumors with DNA-PK overexpression.

Length of Study.

Subjects start Compound 1 with 10 mg BID, receiving daily treatment in 28-day cycles. Compound 1 may be discontinued when there is evidence of tumor progression, but subjects can continue to receive study drug as long as the investigator considers they are deriving benefit. Therapy is discontinued when there is unacceptable toxicity or the subject decides to withdraw from the study.

Enrollment is expected to take about 30 months to complete. Extended treatment for responding subjects and follow-up may last another 3-6 months.

Study Treatments.

Compound 1 will be provided as capsules for oral administration or via an intragastric/jejunal feeding tube, if applicable. Most subjects will start Compound 1 at 10 mg BID.

Overview of Efficacy Assessments.

All treated subjects will be included for the efficacy analysis. The primary efficacy variable is tumor response, based on investigator assessment using the Response Assessment for Neuro-Oncology (RANO) Working Group for GBM. Supplementary efficacy variables (e.g., CTC quantification) will also be examined.

Overview of Safety Assessments.

Primary and exploratory safety variables for this study include AEs, comprehensive panels of clinical laboratory variables (including hematology, chemistry, immunology and thyroid function, and analytes assessing glucose homeostasis), 12-lead triplicate electrocardiograms (ECGs) centrally analyzed, left ventricle ejection fraction (LVEF) assessments, physical examinations, ECOG performance status (ECOG PS) and vital signs.

The Safety Review Committee (SRC) will determine the appropriate dose, doses, or schedule. The SRC will continue to review safety data regularly and make recommendations about the study continuation, as appropriate.

Overview of Pharmacokinetic Assessments.

The PK profiles of Compound 1, and any major metabolites detected, will be determined from serial blood and urine collections, including tumor tissue when available, and correlated with PD outcomes, where possible.

Overview of Pharmacodynamic Assessments.

Exploratory endpoints include mTOR and DNA-PK biomarker inhibition in circulating blood cells, and other tumor cells and/or tissue and aspirates, as available, UV-stimulated DNA-PK activity in skin, histopathologic response and correlations with pharmacogenomic findings. Paired (pre- and during-treatment) tumor biopsies are performed in most subjects with tumor lesions determined by the Investigator to be amenable to biopsy. Analysis will also include apoptosis and proliferation biomarkers in blood, skin, and/or tumor samples when available.

Overview of Predictive Biomarker Assessments.

Mutation and/or protein level of components in relevant pathways including, but not limited to, PI3K/mTOR, DNA damage repair and p53 pathway are explored for identification of potential predictive biomarkers.

In certain embodiments, GBM patients undergoing the clinical protocol provide herein show a positive tumor response, such as inhibition of tumor growth or a reduction in tumor size. In certain embodiments, patients undergoing the clinical protocol provide herein show an improvement in the Response Assessment for Neuro-Oncology (RANO) Working Group. In some such embodiments, the patients' GBM is characterized by MGMT protein expression and/or promoter methylation status. In one such embodiment, the MGMT promoter is hypomethylated. In another embodiment, the MGMT protein is expressed.

A number of references have been cited, the disclosures of which are incorporated herein by reference in their entirety. The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

What is claimed is:

1. A method for treating glioblastoma multiforme characterized by MGMT protein expression and/or promoter hypomethylation status, comprising administering an effective amount of 1-ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof to a patient having glioblastoma multiforme characterized by MGMT protein expression or promoter hypomethylation status.

2. The method of claim 1, wherein the glioblastoma multiforme is that in which the PI3K/mTOR pathway is activated.

3. The method of claim 2, wherein the glioblastoma multiforme is that in which the PI3K/mTOR pathway is activated due to ERBB2 mutation, PTEN mutation or loss, NF1 mutation or loss, PIK3Ca mutation, EGFR mutation or overexpression, Met amplification, PDGFRa activation or amplification, AKT amplification, or a combination thereof.

4. The method of claim 1, wherein said patient is administered about 0.5 mg/day to about 45 mg/day of 1ethyl-7-(2-methyl-6-(1H-1,2,4-triazol-3-yl)pyridin-3-yl)-3,4-dihydropyrazino[2,3-b]pyrazin-2(1H)-one or a pharmaceutically acceptable salt, stereoisomer or tautomer thereof.

5. The method of claim 1, wherein the glioblastoma multiforme is characterized by MGMT protein expression.

6. The method of claim 1, wherein the glioblastoma multiforme is characterized by MGMT promoter hypomethylation.

* * * * *